(12) United States Patent
Wang et al.

(10) Patent No.: US 11,167,006 B2
(45) Date of Patent: Nov. 9, 2021

(54) MULTI-TARGET PEPTIDE MOLECULES OF OPIOID AND NEUROPEPTIDE FF RECEPTOR, PREPARATION FOR MOLECULES, AND APPLICATIONS THEREOF

(71) Applicant: Shanghai Tianci Life Science Development Co., Ltd., Shanghai (CN)

(72) Inventors: Rui Wang, Shanghai (CN); Quan Fang, Shanghai (CN); Zilong Wang, Shanghai (CN); Biao Xu, Shanghai (CN)

(73) Assignee: Shanghai Tianci Life Science Development Co., Ltd., Shanghai (CN)

( * ) Notice: Subject to any disclaimer, the term of this patent is extended or adjusted under 35 U.S.C. 154(b) by 269 days.

(21) Appl. No.: 16/343,873

(22) PCT Filed: Apr. 13, 2017

(86) PCT No.: PCT/CN2017/080350
§ 371 (c)(1),
(2) Date: Jul. 22, 2019

(87) PCT Pub. No.: WO2017/181898
PCT Pub. Date: Oct. 26, 2017

(65) Prior Publication Data
US 2019/0375790 A1 Dec. 12, 2019

(30) Foreign Application Priority Data
Apr. 21, 2016 (CN) .......................... 201610252648.7

(51) Int. Cl.
*A61K 38/08* (2019.01)
*C07K 7/08* (2006.01)
*A61K 38/00* (2006.01)

(52) U.S. Cl.
CPC ................ *A61K 38/08* (2013.01); *C07K 7/08* (2013.01); *A61K 38/00* (2013.01)

(58) Field of Classification Search
None
See application file for complete search history.

(56) References Cited

U.S. PATENT DOCUMENTS

2009/0298755 A1   12/2009   Carr et al.

FOREIGN PATENT DOCUMENTS

| CN | 102241737 A | 11/2011 |
| CN | 102850431 A | 1/2013 |
| CN | 104710508 A | 6/2015 |
| CN | 104877005 A | 9/2015 |
| CN | 106084001 A | 11/2016 |

OTHER PUBLICATIONS

Li et al., British Journal of Pharmacology (2016) 173 1864-1880. (Year: 2016).*
Wang et al., J. Med. Chem. 2016, 59, 10198-10208 (Year: 2016).*
International Search Report (English and Chinese) issued in PCT/CN2017/080350, dated Jul. 5, 2017, 12 pages provided.
Li et al., "BN-9, a chimeric peptide with mixed opioid and neuropeptide FF receptor agonistic properties, produces nontolerance-forming antinociception in mice", British Journal of Pharmacology, accepted Mar. 22, 2016, total 17 pages provided.
Hanif et al., "Chimeric peptide of met-enkephalin and FMRFa: effect of chlorination on conformation and analgesia", Neuroscience Letters, 403 (2006), 5 pages provided.
Foran et al., "A substance P-opioid chimeric peptide as a unique nontolerance-forming analgesic", Proceedings of the National Academy of Sciences of the United States of America, vol. 97 (13), Jun. 20, 2000, 6 pages provided.

* cited by examiner

*Primary Examiner* — Christina M Borgeest
(74) *Attorney, Agent, or Firm* — Hamre, Schumann, Mueller & Larson, P.C.

(57) ABSTRACT

Provided are nine multi-target polypeptides of an opioid and a neuropeptide FF receptor, where an amino acid is replaced on the basis of opioid peptide biphalin- and NPFF-based chimeric peptide BN-9, and acquired are the multi-target polypeptides capable of concurrently activating various opioid and NPFF system receptors.

3 Claims, 11 Drawing Sheets

Specification includes a Sequence Listing.

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE

```
<222> LOCATION: (1)..(1)
<223> OTHER INFORMATION: Tyr or NMe-Tyr
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (4)..(4)
<223> OTHER INFORMATION: Phe or NMe-Phe
<220> FEATURE:
<221> NAME/KEY: MISC_FEATURE
<222> LOCATION: (5)..(5)
<223> OTHER INFORMATION: Gln, or Gly, or Leu, or Met, or D-Met, or
      D-Leu, or D-Ala
<220> FEATURE:
<221> NAME/KEY: MOD_RES
<222> LOCATION: (9)..(9)
<223> OTHER INFORMATION: AMIDATION

<400> SEQUENCE: 1

Xaa Ala Gly Xaa Xaa Pro Gln Arg Phe
1               5

<210> SEQ ID NO 2
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MOD_RES
<222> LOCATION: (1)..(1)
<223> OTHER INFORMATION: METHYLATION
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 2

Tyr Ala Gly Phe Gln Pro Gln Arg Phe
1               5

<210> SEQ ID NO 3
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (9)..(9)
<223> OTHER INFORMATION: AMIDATION

<400> SEQUENCE: 3

Tyr Ala Gly Phe Gln Pro Gln Arg Phe
1               5

<210> SEQ ID NO 4
<211> LENGTH: 9
<212> TYPE: PRT
```

```
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 4

Tyr Ala Gly Phe Gly Pro Gln Arg Phe
1               5

<210> SEQ ID NO 5
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 5

Tyr Ala Gly Phe Leu Pro Gln Arg Phe
1               5

<210> SEQ ID NO 6
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 6

Tyr Ala Gly Phe Met Pro Gln Arg Phe
1               5

<210> SEQ ID NO 7
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (5)..(5)
<223> OTHER INFORMATION: D-Met
<220> FEATURE:
<221> NAME/KEY: MOD_RES
<222> LOCATION: (9)..(9)
<223> OTHER INFORMATION: AMIDATION
```

-continued

```
<400> SEQUENCE: 7

Tyr Ala Gly Phe Met Pro Gln Arg Phe
1               5

<210> SEQ ID NO 8
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MOD_RES
<222> LOCATION: (9)..(9)
<223> OTHER INFORMATION: AMIDATION

<400> SEQUENCE: 8

Tyr Ala Gly Phe Leu Pro Gln Arg Phe
1               5

<210> SEQ ID NO 9
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 9

Tyr Ala Gly Phe Ala Pro Gln Arg Phe
1               5

<210> SEQ ID NO 10
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (9)..(9)
<223> OTHER INFORMATION: AMIDATION

<400> SEQUENCE: 10

Tyr Ala Gly Phe Gly Pro Gln Arg Phe
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: sequence is synthesized
<220> FEATURE:
<221> NAME/KEY: MOD_RES
<222> LOCATION: (9)..(9)
<223> OTHER INFORMATION: AMIDATION

<400> SEQUENCE: 11

Tyr Pro Phe Phe Gly Leu Met
1               5

<210> SEQ ID NO 12
<211> LENGTH: 9
<212> TYPE: PRT
<213> ORGANISM: Artificial Sequence
<220> FEATURE:
<223> OTHER INFORMATION: sequence is synthesized
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: AMIDATION

<400> SEQUENCE: 12

Tyr Ala Gly Phe Gln Pro Gln Arg Phe
1               5
```

MULTI-TARGET PEPTIDE MOLECULES OF OPIOID AND NEUROPEPTIDE FF RECEPTOR, PREPARATION FOR MOLECULES, AND APPLICATIONS THEREOF

TECHNICAL FIELD

The invention belongs to the field of biochemistry peptide drugs and relates to a multi-target polypeptide for simultaneously activating opioid and neuropeptide FF receptors and a preparation method thereof, and the invention also relates to the use of the multi-target polypeptide in the preparation of an analgesic medicine with high efficiency and low side effects.

BACKGROUND ART

Pain is a complex physiological and psychological activity. Pain in a physiological state can be used as a warning that the body is injured, but the pathological chronic pain or persistent severe pain is an unbearable torment for the body. Therefore, analgesia is an important task for medical workers. Clinically, opioid analgesics such as morphine and fentanyl are widely used to treat and alleviate various severe pains, such as post-operative pain and cancer pain. However, opioid analgesics can cause serious adverse reactions such as tolerance, addiction, constipation and respiratory depression, which greatly limit their scope of clinical application.

In recent years, the construction of multi-target opioid molecules has provided new ideas for the development of new high-efficiency and low-side opioid analgesics. Previous studies have shown that based on opioids and the ligands of other systems, a new multi-target drug is constructed to simultaneously act on multiple action sites, and the opioid analgesic activity is exerted while their side effects are reduced by the regulation of other systems. For example, Foran et al. successfully designed and constructed a new class of hybrid peptide ESP7 (Tyr-Pro-Phe-Phe-Gly-Leu-Met-NH2 (SEQ ID NO: 11)) based on opioid peptide EM-2 and tachykinin substance P (SP) (Proc. Nat. Acad. Sci. U.S.A 2000, 97:7621).

A polypeptide is a compound in which amino acids are linked together by peptide bonds. Deletion, increase, configuration change or substitution of amino acids in a polypeptide, modification of amino acid side chains in the polypeptide sequence and the C- or N-terminus of the polypeptide by chemical groups can unpredictably change the original biological activity of the polypeptide compound. Therefore, amino acid modification and substitution of polypeptide compounds to screen for more active compounds is a very important part of the development of polypeptide drugs.

ZL201210098832.2 discloses a novel opioid/NPFF system chimeric peptide BN-9 (Tyr-D-Ala-Gly-Phe-Gln-Pro-Gln-Arg-Phe-NH2 (SEQ ID NO: 12)) based on the high-efficiency opioid ligands Biphalin and neuropeptide FF as chemical templates and the retention of opioid high-efficiency agonists and "key pharmacophores" of neuropeptide FF. A series of pharmacological experiments such as pain modulation, tolerance and gastrointestinal motility in vivo indicate that the chimeric peptide BN-9 based on the opioid peptide Biphalin and NPFF of the present invention exhibits stronger central analgesic activity than morphine, and has the advantages of no pain tolerance and little influence on gastrointestinal motility, and effectively overcomes the side effects such as tolerance and constipation which are common in opioid analgesics. However, the analgesic effect and the potency of the chimeric peptide BN-9 are not ideal.

SUMMARY OF THE INVENTION

The main object of the present invention is to provide a multi-target polypeptide based on opioid and NPFF receptor with high analgesic and low side effects so as to further improve the analgesic effect and onset time of the opioid/NPFF system chimeric peptide BN-9;

another object of the present invention is to provide a method for synthesizing the above multi-target polypeptide;

still another object of the present invention is to use the multi-target polypeptide in the preparation of analgesic drugs by providing analgesic effects of the multi-target polypeptide in receptor agonism, mouse photothermal tail flick and the models of simulated clinical pain as well as pharmacological activity in analgesic tolerance, cardiovascular, gastrointestinal motility and body temperature regulation etc.

(1) Multi-target peptides based on an opioid and neuropeptide FF receptors The multi-target polypeptide of the present invention is a series of multi-target polypeptides capable of simultaneously activating various receptors in opioid and NPFF system obtained by amino acid substitution based on the chimeric peptide BN-9 of the opioid peptide Biphalin and NPFF. Its structural formula is as follows: Its structural formula is as follows:

(SEQ ID NO: 1)
$Xaa_1$-D-Ala-Gly-$Xaa_2$-$Xaa_3$-Pro-Gln-Arg-Phe-$NH_2$, wherein $Xaa_1$ is Tyr or NMe-Tyr; $Xaa_2$ is Phe or NMe-Phe; $Xaa_3$ is Gln, Gly, Leu, Met, D-Met, D-Leu or D-Ala.

When $Xaa_1$ is NMe-Tyr, $Xaa_2$ is Phe, and $Xaa_3$ is Gln, the multi-target polypeptide is labeled as Compound 1.

When $Xaa_3$ is Tyr, $Xaa_2$ is NMe-Phe, and $Xaa_3$ is Gln, the multi-target polypeptide is labeled as Compound 2.

When $Xaa_1$ is Tyr, $Xaa_2$ is Phe, and $Xaa_3$ is Gly, the multi-target polypeptide is labeled as Compound 3.

When $Xaa_1$ is Tyr, $Xaa_2$ is Phe, and $Xaa$; is Leu, the multi-target polypeptide is labeled as Compound 4.

When $Xaa_1$ is Tyr, $Xaa_2$, is Phe, and $Xaa_3$ is Met, the multi-target polypeptide is labeled as Compound 5.

When $Xaa_1$ is Tyr, $Xaa_2$ is Phe, and $Xaa_3$ is D-Met, the multi-target polypeptide is labeled as Compound 6.

When $Xaa_1$ is Tyr, $Xaa_2$ is Phe, and $Xaa_3$ is D-Leu, the multi-target poly peptide is labeled as Compound 7.

When $Xaa_1$ is Tyr, $Xaa_2$, is Phe, and $Xaa_3$ is D-Ala, the multi-target polypeptide is labeled as Compound 8.

When $Xaa_1$ is Tyr, $Xaa_2$ is NMe-Phe, and $Xaa_3$ is Gly, the multi-target polypeptide is labeled as Compound 9.

The amino acid sequences of the above compounds are shown in Table 1:

TABLE 1

Amino acid sequences of multi-target polypeptides of opioid and neuropeptide FF receptor

| Compound | Amino acid sequences | |
|---|---|---|
| Compound 1 | NMe-Tyr-D-Ala-Gly-Phe-Gln-Pro-Gln-Arg-Phe-NH$_2$ | (SEQ ID NO: 2) |
| Compound 2 | Tyr-D-Ala-Gly-NMe-Phe-Gln-Pro-Gln-Arg-Phe-NH$_2$ | (SEQ ID NO: 3) |
| Compound 3 | Tyr-D-Ala-Gly-Phe-Gly-Pro-Gln-Arg-Phe-NH$_2$ | (SEQ ID NO: 4) |
| Compound 4 | Tyr-D-Ala-Gly-Phe-Leu-Pro-Gln-Arg-Phe-NH$_2$ | (SEQ ID NO: 5) |
| Compound 5 | Tyr-D-Ala-Gly-Phe-Met-Pro-Gln-Arg-Phe-NH$_2$ | (SEQ ID NO: 6) |
| Compound 6 | Tyr-D-Ala-Gly-Phe-D-Met-Pro-Gln-Arg-Phe-NH$_2$ | (SEQ ID NO: 7) |
| Compound 7 | Tyr-D-Ala-Gly-Phe-D-Leu-Pro-Gln-Arg-Phe-NH$_2$ | (SEQ ID NO: 8) |
| Compound 8 | Tyr-D-Ala-Gly-Phe-D-Ala-Pro-Gln-Arg-Phe-NH$_2$ | (SEQ ID NO: 9) |
| Compound 9 | Tyr-D-Ala-Gly-NMe-Phe-Gly-Pro-Gln-Arg-Phe-NH$_2$ | (SEQ ID NO: 10) |

(I) Preparation of Multi-Target Polypeptides of Opioid and Neuropeptide FF Receptors The method for synthesizing the multi-target polypeptide comprises the following steps:

i. Synthesis of Polypeptide i.i resin pretreatment: Rink-Amide-MBHA resin is stifled in dichloromethane, the resin is fully swelled, and the solvent is evaporated under reduced pressure; finally, DMF is added for washing.

i.ii removal of Fmoc group protection: in the swelled resin in which the solvent therein is evaporated, a mixed solution of hexahydropyridine, 1,8-diazabicycloundecyl-7-ene and DMF is added at a volume ratio of 1:1:98, stirred for 5 minutes, then evaporated, repeated for 3 times; finally DMF is added for washing, detected by indene, to obtain a resin with Fmoc group protection being removed.

i.iii condensation of amino acids: N-α-Fmoc protected amino acid Fmoc-AA-OH, N-hydroxybenzotriazole and O-benzotriazole-N,N,N,N'-teramethylurea-hexafluorophosphate are completely dissolved in DMF in turn, and then diisopropylethylamine is added, mixed to obtain a mixed solution; then added into the resin with the Fmoc group protection being removed obtained in step i.ii, and stirred for 60 min in argon, and the solvent is evaporated; repeatedly washed with DMF, and evaporated, and the Fmoc group protection is removed according to the process in step i.ii after indene-detection, to obtain a peptide resin with the Fmoc protecting group being removed.

The molar ratio of Fmoc-AA-OH and the resin with the Fmoc group protection being removed is 1:2~1:5. The molar ratio of Fmoc-AA-OH, N-hydroxybenzotriazole, O-benzotriazole-N,N,N',N'-tetramethylurea-hexafluorophosphate and diisopropylethylamine is 3:1:1:2.

i.iv Extension of the Peptide Chain

According to the structural design of the polypeptide compounds 1-9, the N-α-Fmoc protected amino acid is selected from the C-terminus in turn, and the resin with the Fmoc protecting group being removed obtained in step iii is subjected to the condensation of the peptide chain according to the process of step i.iii, to obtain a side chain fully protected peptide resin. The amino acids used are Fmoc-Tyr (tBu)—OH, Fmoc-NMe-Tyr(tBu)—OH, Fmoc-D-Ala-OH, Fmoc-Gly-OH, Fmoc-Phe-OH, Fmoc-NMe-Phe —OH, Fmoc-Gln(Trt)-OH, Fmoc-Gly-OH, Fmoc-Leu-OH, Fmoc-D-Leu-OH, Fmoc-Met-OH, Fmoc-D-Met-OH, Fmoc-Pro-OH, Fmoc-Arg(Pbt)-OH, Fmoc-Phe-OH, Fmoc-Ala-OH, Fmoc-D-Ala-OH.

ii, Cleavage of the Polypeptide from the Resin the peptide resin obtained in step i.iv is washed alternately with DCM and MeOH, and the solvent is sufficiently evaporated, then a cleavage agent (the cleavage agent is a solution formed by mixing trifluoroacetic acid, triisopropylsilane and water at a volume ratio of 95:2,5:2,5) is added, and incubated for 2 to 3 hours at room temperature; filtered, and the filtrate is sufficiently evaporated under reduced pressure at a temperature not higher than 37° C. and then precipitated with ethyl ether at not higher than −10° C.; the supernatant is aspirated, water is added to sufficiently dissolve the precipitate, the ethyl ether is removed from the aqueous phase, and the aqueous phase is freezed and dried to obtain a white crude peptide solid powder.

iii. desalination and Purification of the Polypeptide acetic acid solution with a volume concentration of 15-20% is used as a mobile phase, passed through a Sephadex G25 cross-linked dextran gel column the main peak is collected by a UV detector and then freezed and dried to obtain a desalted peptide compound; and then the desalted peptide compound separated and purified by reversed-phase high performance liquid chromatography column, and the main peak of the sample is collected after separation to obtain the multi-target polypeptide product.

The chemical characterization results of the above synthesized series of multi-target poly peptides are shown in Table 2:

TABLE 2

Chemical characterization of opioid and neuropeptide FF receptor multi-target polypeptides

| compound | Chromatographic analysis retention time HPLC $t_R$ (min) | | High resolution mass spectrometry (MD-TOF-MS) m/z (M + H*) | | Melting point |
| --- | --- | --- | --- | --- | --- |
| | System 1 | System 2 | Calculated value | Detected value | MP(° C.) |
| compound 1 | 13.945 | 12.842 | 1126.54 | 1126.57 | 147-149 |
| compound 2 | 13.499 | 14.729 | 1126.54 | 1126.58 | 146-148 |
| compound 3 | 14.808 | 13.542 | 1041.50 | 1041.53 | 145-146 |
| compound 4 | 15.590 | 14.086 | 1097.56 | 1097.59 | 144-146 |
| compound 5 | 16.085 | 14.512 | 1115.52 | 1115.55 | 144-145 |
| compound 6 | 17.241 | 15.530 | 1115.52 | 1115.55 | 144-146 |
| compound 7 | 18.535 | 16.447 | 1197.56 | 1197.59 | 146-148 |
| compound 8 | 15.638 | 14.203 | 1055.52 | 1055.54 | 147-149 |
| compound 9 | 14.850 | 13.613 | 1055.50 | 1055.54 | 147-149 |

Note:
System 1: Gradient elution system 1 is: 10-100% acetonitrile/water (0.1% TFA) (completed in 30 minutes), flow rate: 1 mL/min, detection wavelength: 220 nm, analytical chromatographic column: XBridge ™ BEH 130Prep $C_{18}$, 4.6 mm × 250 mm; System 2: Gradient elution system 2: 10-80% acetonitrile/water (0.1% TFA) (completed in 30 minutes), flow rate: 1 mL/min, detection wavelength: 220 nm, the analytical chromatographic column: XBridge ™ BEH 130Prep $C_{18}$, 4.6 mm × 250 mm.

(3) Activity Detection of Opioid and Neuropeptide FF Receptor Multi-Target Peptides In Vitro cAMP Function Test Experiments In HEK293 cells stably expressing Mu-, Delta-, Kappa-opioid receptors and $NPFF_1$ and $NPFF_2$ receptors, agonistic activities the multi-target polypeptide of the opioid and NPFF receptor against these five receptors are tested by detecting the regulation of the accumulation of intracellular cyclic adenosine monophosphate (cAMP) caused by Forskolin.

(1) Experimental Method for Detecting cAMP Function

HEK293 cells stably expressing Mu-, Delta-, Kappa-opioid receptors and $NPFF_1$ and $NPFF_2$ receptors were seeded in 24-well plates at a density of 120,000/well and cultured for 24 hours in a $CO_2$ incubator. At the beginning of the experiment, the cell culture fluid was replaced with a pre-warmed serum-free medium containing 1 mM IBMX, and incubated for 10 min at 37° C. Then, in each well was added different concentrations of the test drug and 5 μM forskolin (final concentration), and incubated for 30 min at 37° C. After the completion of the incubation, the solution in each well was aspirated completely, and the cells were lysed by using 500 μL of 0.2 M hydrochloric acid and incubating for 30 min at room temperature. After the completion of the lysis, 10 μL of 10 M MOH solution was added to each well to neutralize the lysate. The solution in each well was evenly pipetted, transferred to a centrifuge tube, and centrifuged at 12,000 rpm for 2 min. 50 μL of the supernatant was pipetted into a clean centrifuge tube, and 100 μL of 60 ug/μL of PKA was added, and 100 μL of TE cAMP buffer was added to the blank control group. 50 μL of 0.5 μCi [$H^3$]cAMP was added to each of the above centrifuge tube, mixed rapidly, and incubated at 4° C. for more than 2 hours. After the incubation, 100 μL of activated carbon suspension was added to each tube, vortexed uniformly, placed in an ice bath for 1 min, and centrifuged at 5000 rpm for 4 min. After centrifugation, 200 μL of the supernatant aspirated from each tube was added to a 24-well plate, and 700 μL of scintillation fluid was added to each well, and then the 24-well plate was sealed with a gel film, and measured with a scintillator after standing for 3 hours.

(2) Calculate the Inhibition Value of cAMP

The inhibitory effect on cAMP is expressed as the inhibition percentage of Forskolin-induced intracellular cAMP accumulation by the drug (% control), % control=(Forskolin-treated cAMP content—the cAMP content co-processed with the test drug and Forskolin)/(Forskolin-treated cAMP content—solvent-treated cAMP content). The relevant % control data is expressed as mean±standard error (Means±S.E.M.). The dose-response relationship of the drug was statistically analyzed by nonlinear regression model, using the statistical software GraphPad. Prism version 5.0, the $EC_{50}$ values of the inhibition of intracellular cAMP accumulation caused by Forskolin by the multi-target peptide of this opioid and NPFF receptor were calculated respectively, and the results are shown in Table 3.

In the HEK293 cell line stably expressing the Mu-opioid receptor, Compounds 1-9 were able to dose-dependently inhibit the accumulation of cAMP caused by forskolin. It is indicated that Compounds 1-9 have agonistic activity on Mu-opioid receptors. In the HEK293 cell line stably expressing Kappa-opioid receptor, all compounds except Compound 7 and Compound 8 were able to dose-dependently inhibit forskolin-induced cAMP accumulation. It is indicated that compounds 1-6 and 9 have agonistic activity on Kappa opioid receptors. In the HEK293 cell line stably expressing Delta-opioid receptor, compounds 1-9 could inhibit the accumulation of cAMP induced by forskolin in a dose-dependent manner, indicating that compounds 1-9 have agonistic activity on the Delta-opioid receptor, In the HEK293 cell line stably expressing the $NPFF_1$ receptor, both Compounds 1-5 and 9 were able to dose-dependently inhibit forskolin-induced cAMP accumulation. It is indicated that both compounds 1-5 and compound 9 have agonistic activity on the $NPFF_1$ receptor. Compounds 6-8 have weak agonistic effects on the $NPFF_1$ receptor, so that their complete dose-response curves cannot be measured, and their $EC_{50}$ values could not be calculated. In the HEK293 cell line stably expressing the $NPFF_2$ receptor. Compounds 1-9 were able to dose-dependently inhibit forskolin-induced cAMP accumulation. These compounds 1-9 have agonistic activity on the $NPFF_2$ receptor. The $EC_{50}$ values of Compounds 1-9 for the five receptors in the cAMP function detection experiments are shown in Table 3. In summary, Compounds 1-9 have an agonistic effect on various receptors in the opioid and NPFF systems, and are a class of multi-target polypeptides of opioid and NPFF receptors.

TABLE 3 cAMP function experiments of multi-target polypeptides of opioid and neuropeptide FF receptor

| | $IC_{50}$ value (M) (95% confidence interval) | | | | |
|---|---|---|---|---|---|
| compound | μ-OR | κ-OR | δ-OR | $NPFFR_1$ | $NPFFR_2$ |
| compound 1 | 196.2 (65.79 to 584.9) | 2586 (2149 to 3111) | weak | 927.7 (290.7 to 2961) | 132.2 (31.58 to 553.1) |
| compound 2 | 20.10 (16.54 to 24.43) | 31.0 (27.10 to 35.47) | 159.7 (77.24 to 330.2) | 289.1 (66.31 to 1261) | 271.7 (102.8 to 718.4) |
| compound 3 | 28.42 (3.754 to 215.2) | 1631 (1250 to 2128) | 898.3 (591.4 to 1364) | 880.7 (139.6 to 5556) | 184.8 (19.10 to 1788) |
| compound 4 | 250.2 (84.93 to 737.0) | 120.3 (80.83 to 179.2) | 49.27 (25.90 to 93.71) | 54.38 (8.86 to 333.8) | 258.7 (53.18 to 1259) |
| compound 5 | 126.9 (75.58 to 213.1) | 239.8 (111.6 to 515.2) | 38.77 (28.01 to 53.68) | 301.3 (66.94 to 1357) | 86.98 (12.51 to 604.8) |
| compound 6 | 409.0 (251.0 to 666.4) | 2457 (475.8 to 12690) | 119.9 (92.02 to 156.2) | weak | 318.2 (66.34 to 1526) |
| compound 7 | 583.3 (674.7 to 908.2) | weak | 56.86 (32.83 to 98.50) | weak | 651.4 (204.2 to 2078) |
| compound 8 | 248.6 (167.8 to 368.3) | weak | 810.2 (334.0 to 1965) | weak | 5012 (951.8 to 26390) |
| compound 9 | 38.63 (26.83 to 51.61) | 1421 (830.8 to 2431) | 574.7 (370.2 to 892.3) | 973.4 (230.5 to 41111) | 310.8 (150.1 to 643.2) |

2. Photothermal Tail Flick Analgesia Experiment

After the drug was injected into the lateral ventricle, intrathecal, subcutaneous, and intraperitoneal, the modulating activity on pain was measured by the photothermal tail flick test in mouse.

(1) Mode of Administration

In the lateral ventricle administration, the lateral ventricle tube-buried surgery of the mouse should be performed in advance to ensure the accuracy of the drug injection site. A brain stereotaxic instrument was used in the lateral ventricle tube-buried surgery of the mouse. Male mice of Kunming strain, weighing 21±2 g; brain stereotaxic instrument is Jiangwan I. After the mice were anesthetized with sodium pentobarbital (i.p., 80 mg/kg mouse body weight), the hair in the head surgery area of the mouse was cut off and the mouse was placed on the brain stereotactic instrument and fixed. The surgery area was disinfected with iodophor, the scalp was opened along the sagittal suture to reveal the skull and the position of the anterior fontanelle can be found. 3 mm backward and 1 mm left/right from the anterior fontanelle, the upper position of the lateral ventricle can be found. A self-made stainless steel tube (a section of 24-gauge, which is connected to a small section of PE-10 tube) is inserted 3 mm downward according to the above position, which is the lateral ventricle. A section of stainless steel string (28-gauge) is inserted into the above-mentioned steel tube to prevent cerebrospinal fluid spillage and foreign matter infection and block the steel pipe. The steel tube is fixed with medical dental powder and glue, and after solidification, the wound is sutured. After the surgery, the mice were recovered tier 4 days, and the follow-up experiment was started on the 5th day. Surgical instruments, stainless steel tubes, etc. involved in the experiment need to be disinfected before the surgery. The mouse lateral ventricle was injected with 4 μl of the drug each time, and then the steel tube was rinsed with 1 μl of physiological saline.

Spinal cord level administration is performed by intrathecal injection in conscious mice, and the specific procedure is described in the method reported by Hylden and Wilcox (Eur. J. Pharmacol. 1980, 67: 313). A 25 μL microinjector was inserted directly into the subarachnoid space between L5 and L6. When the arachnoid was punctured, the mouse had a violent and obvious tail flick movement or the tail was "S" shaped, and saline or drug was injected into the subarachnoid space at a rate of 5 μl/10 sec.

The intraperitoneal administration was directly injected using a 1 mL syringe at an injection volume of 10 μl/g body weight. At the time of injection, the mouse was held by left hand with their abdomen facing up and the head was at low position while the tail was at high position. The side of the midline of the abdomen was taken, the needle hole of the syringe was upward, the needle tip penetrates into the skin in a direction less than 20 degrees, the needle tip was slightly pushed in the direction of the mouse head and sticking abdominal wall, and then punctures into the abdominal cavity in the direction of 45 degrees, and was withdrawn to confirm that it has not been pierced into the blood vessel or the intestine, afterwards the drug solution is slowly pushed out.

Subcutaneous injection was also administered directly using a 1 mL syringe in an injection volume of 10 μl/g body weight. At the time of injection, the neck and tail of the mouse were fixed in the left hand, and the head and body were inclined downward at 45 degrees. The needle hole of the syringe is upward, the needle tip is slowly pierced into the skin on the right side of the back center line at an angle of less than 20 degrees, and the needle tip is lightly picked up to confirm that there is no piercing, afterwards the drug solution is slowly pushed out.

(2) Mouse Photothermal Tail Flick Experiment

Male mice of Kunming strain were used to detect the effects of drugs on pain perception using a photothermal tail flick instrument. The ambient temperature is controlled at 22±1° C., and the experimental animals are free to eat and drink. The basic tail flick incubation period (3-5 seconds) was determined prior to administration, and mice that were too sensitive or dull were discarded. The tail flick incubation period at different time points after administration were recorded. In order to prevent scald, 10 seconds is set as the longest tail flick incubation period, and the tail flick time which is more than 10 seconds is counted as 10 seconds.

(3) Calculating the MPE and $ED_{50}$ Values of Drug Analgesic Effects

The pain modulation effect was evaluated using the MPE (maximum possible effect) MPE (%)=100×[(pain threshold after administration−basal pain threshold)/(10 seconds−basal pain threshold)]. The $ED_{50}$ value indicates the drug dose at which the drug produces a 50% maximum analgesic effect. Using the statistical software GraphPad Prism version 5.0, analgesic $ED_{50}$ values and 95% confidence intervals were calculated by the MPE (%) values at the maximum analgesic effect time points, respectively.

$ED_{50}$ of an analgesic effect on acute pain caused by photothermal therapy after administration in lateral ventricle is shown in Table 4. In the mouse tail flick model, all of these 9 compounds can produce significantly analgesic effect on acute thermal pain after being administrated into the lateral ventricle. Except for compound 1, the analgesic of the other eight compounds were less than 1 nmol, especially the analgesic $ED_{50}$ value of compound 9 was only 16.3 pmol, which was 23.9 times of BN-9 (0.39 nmol ZL201210098832.2).

In addition, we further investigated the analgesic effect of Compound 9 when administrated at the spinal cord and systemic levels, as shown in FIGS. 1-3. Intrathecal administration of compound 9 can produce dose-dependent analgesia for acute pain caused by photothermal therapy, its analgesic $ED_{50}$ value was 1.33 pmol, and the maximum analgesic MPE value at 5 pmol was 94.7%, which was 218 imes of that of BN-9 (019 nmol, Z1201210098832.2), Systemic levels administration of compound 9 also caused a dose-dependent analgesic effect on acute pain caused by photothermal therapy. Subcutaneous levels of analgesia $ED_{50}$ values were lower than abdominal levels of analgesia. $ED_{50}$ values, 0.2279 mg/kg and 26.58 mg/kg, respectively.

TABLE 4

Analgesic activity produced by lateral ventricle injection of multi-target polypeptides of opioid and neuropeptide FF receptor

| compound | $ED_{50}$ value (nmol) (95% confidence interval) |
| --- | --- |
| compound 1 | 1.2980 (1.2000 to 1.4050) |
| compound 2 | 0.3862 (0.3590 to 0.4154) |
| compound 3 | 0.4172 (0.3798 to 0.4583) |
| compound 4 | 0.1865 (0.1509 to 0.2304) |
| compound 5 | 0.2957 (0.2637 to 0.3338) |
| compound 6 | 0.3986 (0.3716 to 0.4275) |
| compound 7 | 0.4367 (0.3865 to 0.4934) |
| compound 8 | 0.3361 (0.2864 to 0.3944) |
| compound 9 | 0.0163 (0.0145 to 0.0182) |

3. Analgesic Tolerance Test

The mice were injected with the drug in the lateral ventricle of the mice for six consecutive days or in the subcutaneous of the mice for eight consecutive days, and their analgesic tolerance were detected by photothermal tail flick method, and the pharmacological activity of the compounds of the present invention in analgesic tolerance was further explored.

(1) Experimental Method for Pain Tolerance in Mice

In male mice of Kunming strain, the drug was injected continuously in the lateral ventricle for six days, once a day, and the effect of continuous injection of drugs on the pain sensation was detected by a photothermal tail flick instrument. The ambient temperature is controlled at 22±1° C., and the experimental animals are free to eat and drink. The test drug was injected into the lateral ventricle of the mouse for 6 consecutive days, 4 μl per injection. The basic tail flick incubation period (3-5 seconds) was measured before the first day of drug injection, and those mice that were too sensitive or dull were discarded. The tail flick incubation period of 5, 10, 15, 20, 30 min after administration on the first and sixth days was recorded in the experiment. To prevent scald on the tail of the mouse, the maximum tail flick incubation period was set as 10 seconds, In addition, we further studied the tolerance of subcutaneous administration of compound 9 and morphine in the photothermal tail flick test. The ambient temperature is controlled at 22±1° C., and the experimental animals are free to eat and drink. First, the basic tail flick incubation period (3-5 seconds) of the mice was measured before administration, and then compound 9 or morphine was administered subcutaneously for eight consecutive days. The tail flick incubation period of 10, 15 and 20 minutes after daily administration were recorded. To prevent scald on the tail of the mouse, the maximum tail flick incubation period was set as 10 seconds.

(2) Statistics of Tolerance Experiment Data

The experimental data is expressed by MPE (maximum possible effect), MPE (%)=100×[(pain threshold after administration−basal pain threshold)/(10 seconds−basal pain threshold)]. The analgesic tolerance of the drug was compared using the MPE value at the time of maximum analgesic effect of the drug. MPE data was expressed as mean±standard error (Means±S.E.M.). The difference in the analgesic effect of continuous administration in the lateral ventricle of the mice for six days was statistically analyzed by the paired T test, and the difference in the analgesic effect of subcutaneous continuous administration for eight days was analyzed by One-way analysis of variance (one-way ANOVA's Tukey HSD test) for statistics, and ***$P<0.001$ indicates a significant difference from the analgesic effect of the drug injected on the first day. The experimental results are shown in FIGS. 4-5.

There were 7-10 mice in each group, and the saline group was a blank control group. As shown in FIG. 4, the dose of the drug for lateral ventricle administration was 3 times $ED_{50}$ of the drug, respectively, and 4 nmol of morphine can produce considerable analgesic effect. The mice did not produce analgesic activity after the mice were injected with saline in the lateral ventricle for six consecutive days. Compared with the saline control group, the injection of Compounds 1-9 and morphine in the lateral ventricle significantly prolonged the tail flick incubation period of the mice on the first day. Morphine was continuously injected into the lateral ventricle of mice for six days, and the induced analgesic effect was reduced from 86.97% on the first day to 36.15%, indicating that continuous lateral ventricle injection of morphine can significantly cause analgesia tolerance. Compared with morphine, the MPE value of analgesia was not significantly changed after 6 days of continuous lateral ventricle injection of compounds 1-9, indicating that compounds 1-9 did not produce analgesic tolerance. As shown in FIG. 5, the analgesia effect of subcutaneous injection of 10 mg/kg of Compound 9 in mice was equivalent to that of an equal dose of morphine. The analgesic effect of continuous injection of morphine significantly reduced from day 4, resulting in analgesia tolerance. Compared with morphine, Compound 9 was administered subcutaneously for eight consecutive days and its analgesic effect was not significantly different from that of the first day. It further verified that Compound 9 had no analgesia tolerance, indicating that Compound 9 may be effective in avoiding the tolerated side effects common to opioid analgesics.

4. The Analgesic Effect of Compound 9 in Formalin Model Pain (1) Method for Detecting Formalin Pain in Mice The mice were placed in a transparent organic glass box (20×20×30 cm) to accommodate the environment for 10-15 min; a mirror tilted at 30 degrees was placed underneath to facilitate observation of the mouse's foot reaction. After adaptation, the mice were administered in lateral ventricle, intrathecally or intraperitoneally. 5 minutes after administration, 20 μL of a 5% formalin solution was subcutaneously injected into the toes of the right hind paw of the mice, and quickly placed back in the observation box. Timing was started, and the time when the mouse was licking, biting and shaking the injected paw during 0-5 minutes and 15-30 minutes after the injection of the formalin solution were recorded respectively.

(2) Formalin Pain Test Data Statistics

The experimental data was expressed by MPE (maximum possible effect), MPE (%)=100×[(licking paw time in saline group−licking paw time in drug group)/licking paw time in saline group]. The relevant MPE data were expressed as mean±standard error Means±S.E.M.), the data for differences between groups treated with different drug concentrations were analyzed by one-way ANOVA (Bonferroni test in one-way ANOVA) for statistics and analysis, *P<0.001 represents that there was a significant difference between the MPE value of the drug-treated group and that of the saline group. The experimental results are shown in FIGS. 6-8**.

The saline group was a blank control group, and the number of animals in each group was 8-9. The first phase pain of formalin pain is acute pain caused by chemical stimulation, and the second phase is inflammatory pain. As shown in FIGS. 6-8, lateral ventricle, intrathecal and intraperitoneal injection of compound 9 in mouse can dose-dependently inhibit formalin-induced first-phase acute pain and second-phase inflammatory pain, indicating that Compound 9 has potential application value in the treatment of chemical stimulation pain and inflammatory pain.

The $ED_{50}$ value indicates the drug dose at which the drug produces a 50% maximum analgesic effect. Using the statistical software GraphPad Prism version 5.0. the $ED_{50}$ values and 95% confidence intervals for analgesia induced by the lateral ventricle injection were calculated based on MPE (%) values, respectively. The relevant data is shown in Table 5.

TABLE 5

Analgesic effect of compound 9 on formalin pain

| administration route | $ED_{50}$ value (95% confidence interval) | |
|---|---|---|
| | first phase pain | second phase pain |
| lateral ventricle (i.c.v.) (pmol) | 18.80 (15.97 to 22.12) | 103.4 (96.02 to 111.3) |
| intrathecal (i.t.) (pmol) | 37.69 (35.53 to 39.99) | 55.04 (51.26 to 59.10) |
| intraperitoneal (i.p.) (mg/kg) | 8.855 (7.573 to 10.35) | 10.92 (9.632 to 12.39) |

The results in Table 5 indicate that the lateral ventricle injection of Compound 9 has an analgesic $ED_{50}$ value of 18.8 and 103.4 pmol in formalin first phase pain and second phase pain, respectively, while the lateral ventricle injection of BN-9 has an analgesic $ED_{50}$ value of 0.12 and 1.14 nmol in formalin first phase pain and second phase pain, respectively (Br J Pharma. col, 2016, doi: 10.1111/bph. 13489). According to the $ED_{50}$ value of formalin pain, the analgesic effect of Compound 9 in the first phase pain and the second phase pain of formalin pain were calculated as 6.3 times and 11.0 times of that of BN-9, respectively.

5. Analgesic Effect of Compound 9 in the Visceral Pain Model of Acetic Acid Writhing (1) Detection Method for Acetic Acid Writhing Test in Mouse The mice were placed in a transparent polymethyl methacry late box (20×20×30 cm) and adapted to the environment for 10-15 min; after the adaptation, compound 9 was administered intrathecally, intraperitoneally or subcutaneously to the mice. After 5 min, the mice were intraperitoneally injected with 10 ml/kg of 0.6% acetic acid solution, 5 min. after the intraperitoneal injection of acetic acid solution, the writhing response of the mice was recorded for 10 min. The mice developed characteristic reactions such as twisting of the trunk, concave in the abdomen, elevation of the buttocks and extension of the hind limbs, which were recorded as a writhing reaction.

(2) statistics of Experiment Data of Acetic Acid Writhing

The experimental data was expressed by MPE (maximum possible effect), MPE (%)=100×[(the number of writhing bodies in the physiological saline group− the number of writhing bodies in the drug group)/the number of writhing bodies in the physiological saline group]. The relevant MPE data were expressed as mean±standard error (Means±S.E.M.), the data for differences between groups treated with different drug concentrations were analyzed by one-way ANOVA (Bonferroni test in one-way ANOVA) for statistics and analysis, *P<0.001 represents that there was a significant difference between the MPE value of the drug-treated group and that of the saline group. The experimental results are shown in FIGS. 9-11**.

The saline group was a blank control group, and the number of animals in each group was 8-9. As shown in FIGS. 9-11, compound 9, whether it is intrathecal, intraperitoneal or subcutaneously injected into the mice, can produce analgesic effects on visceral pain induced by intraperitoneal injection of acetic acid solution in a dose-dependent manner. This indicates that Compound 9 has potential application value in the treatment of visceral pain.

The $ED_{50}$ value indicates the drug dose at which the drug produces a 50% maximum analgesic effect. Using the statistical software GraphPad Prism version 5.0. the $ED_{50}$ values and 95% confidence intervals for analgesia induced by injection at different levels were calculated based on MPE (%) values, respectively. The relevant data is shown in Table 6.

TABLE 6

Analgesic effect of compound 9 on acetic acid-induced visceral pain

| administration route | $ED_{50}$ value (95% confidence interval) |
|---|---|
| intrathecal (i.t.) (pmol) | 0.657 (0.595 to 0.727) |
| intraperitoneal (i.p.) (mg/kg) | 0.721 (0.594 to 0.875) |
| subcutaneous (s.c.) (mg/kg) | 0.789 (0.702 to 0.887) |

6. Analgesic Effect of Compound 9 in Postoperative Pain Model (1) Detection Method for Postoperative Pain in Mice The postoperative pain in mice was detected mainly by an electronic Von Frey tenderness instrument. The basic pain threshold of normal mice was first determined, and then the mice were anesthetized with isoflurane. With the back facing up, the right hind paw of the mouse was fixed and disinfected with iodine solution. A 5 mm longitudinal incision was made with a No. 11 blade at 2 mm from the ankle to expose the plantaris, blood vessels and fascia, and the wound was sutured using a 4-0 surgical suture and a small suture needle, and the wound is coated with erythromycin ointment. The mechanical pain sensitivity value of the surgical foot of the mice was measured 6 h after the surgery, and then compound 9 was intrathecally or intraperitoneally given, and the mechanical pain threshold at different time points after administration were recorded.

(2) Data Statistics for Postoperative Pain

The experimental data were expressed as mean±standard error (Means±S.E.M.), and the data for differences between groups treated with different drug concentrations were analyzed by one-way ANOVA (Bonferroni test in one-way ANOVA) for statistics and analysis, *P<0.001 represents that there was a significant difference between the MPE value of the drug-treated group and that of the saline group. The experimental results are shown in FIGS. 12-13**.

The ED$_{50}$ value indicates the drug dose at which the drug produces a 50% maximum analgesic effect. First, the maximum analgesic effect (MPE) was calculated, MPF. (%)=100×[(pain threshold after administration–postoperative pain sensitivity value)/(basic pain threshold–postoperative pain threshold)]. Then, using the statistical software GraphPad Prism version 5.0, the ED$_{50}$ value and the 95% confidence interval for analgesia induced by intrathecal and intraperitoneal administration were calculated based on MPE (%) values, respectively.

The saline group was a blank control group, and the number of animals in each group was 8-9. As shown in FIGS. 12-13, compound 9 trathecally and intraperitoneally injected in mice can produce analgesic effects on postoperative pain in mice in dose-dependent manner. The ED$_{50}$ values of analgesia of compound 9 for postoperative pain in mice after intrathecal and intraperitoneal administration were 8.63 (6.70-11.11) pmol and 26.15 (22.62-30.23) mg/kg, respectively. It is indicated that compound 9 has potential application value in the treatment of surgical pain.

7. Analgesic Effect of Compound 9 in Inflammatory Pain Model (1) Detection Method for Inflammatory Pain in Mice Inflammatory pain in mice was measured using a hot stinging apparatus and an electronic Von Frey tenderness instrument, and the basal pain threshold of normal mice was firstly determined. Then 20 μl of 2% Carrageenan solution or CFA solution was injected subcutaneously into the mouse paw. The thermal and mechanical pain sensitivity value values of the injected paw in mice were tested after 24 hours (Carrageenan) or 4 days (CFA), and then compound 9 was administered into lateral ventricle, intrathecally or subcutaneously, and the pain threshold at different time points after administration were recorded.

(2) Data Statistics

The experimental data were expressed as mean±standard error (Means±S.E.M.), and the data for differences between groups treated with different drug concentrations were analyzed by one-way ANOVA (Bonferroni test in one-way ANOVA) for statistics and analysis, *P<0.001 represents that there was a significant difference between the pain threshold value of the drug-treated group and that of the saline group. The experimental results are shown in FIGS. 14-16**, The ED$_{50}$ value indicates the drug dose at which the drug produces a 50% maximum analgesic effect, First, the maximum analgesic effect (MPE, maximum possible effect) was calculated firstly, MPE (%)=100×[(pain threshold after administration–pain sensitivity value in injected paw)/(basic pain threshold–pain sensitivity value in injected paw)]. The ED$_{50}$ value and the 95% confidence interval for analgesia induced by lateral ventricle, intrathecal and subcutaneous administration were then respectively calculated based on MPE (%) values using the statistical software GraphPad Prism version 5.0.

The saline group was a blank control group, and the number of animals in each group was 8-9. As shown in FIGS. 14-16, the lateral ventricle, intrathecal and subcutaneous injection of compound 9 in mice can produce analgesic effects on inflammatory pain in mice in a dose-dependent manner. The analgesic ED$_{50}$ values were 5.20 (2.06-13.10) pmol, 2.98 (2.50-3.54) pmol and 3.24 (2.81-3.74) mg/kg, respectively. It is indicated that compound 9 has potential application value in the treatment of inflammatory pain.

8. Analgesic Effect of Compound 9 in a Neuralgia Model (1) Detection Method for Mouse CCI Neuralgia Model The chronic compression model of the sciatic nerve (CCI) was mainly used for the mouse neuralgia. The detection method uses thermal tingling instrument and electronic Von Frey tenderness instrument to simultaneously detect thermal pain and mechanical pain. Firstly, the basic pain threshold of thermal pain and mechanical pain in normal mice were determined respectively. The mice were then anesthetized with sodium pentobarbital (i.p., 80 mg/kg mouse body weight) and the mice were fixed in the prone position. The right sciatic nerve was exposed and 3 mild ligation rings were made around the sciatic nerve using a 4-0 chromic catgut, 1 mm intervals. The ligation intensity is preferably a slight tremor in the right hind leg. On the 10th day after surgery, the thermal pain sensitivity value of the right hind paw of the mouse was measured, and then compound 9 was intrathecally or subcutaneously administered, and the thermal pain threshold at different time points after administration were recorded. On the 11th day after surgery, the mechanical pain sensitivity value of the right hind paw of the mouse was measured, and then Compound 9 was intrathecally or subcutaneously administered, and the mechanical pain threshold at different time points after administration were recorded.

(2) Data Statistics of Neuralgia in CC1 Mice

The experimental data were expressed as mean±standard error (Means±S.E.M.), and the data for differences between groups treated with different drug concentrations were analyzed by one-way ANOVA (Bonferroni test in one-way ANOVA) for statistics and analysis, P<0.01, *P<0.001 represents that there was a significant difference between the pain threshold value of the drug-treated group and that of the saline group. The experimental results are shown in FIGS. 17-20.

The ED$_{50}$ value indicates the drug dose at which the drug produces a 50% maximum analgesic effect. First, the maximum analgesic effect (MPE) was calculated, MPE (%)=100×[(pain threshold after administration–pain sensitivity value of the hind paw in surgical side)/(basic pain threshold–pain sensitivity value of the hind paw in surgical side)]. The ED$_{50}$ value and the 95% confidence interval for analgesia induced by intrathecal and subcutaneous administration were then respectively calculated based on MPE (%) values using the statistical software GraphPad Prism version 5.0.

The saline group was a blank control group, and the number of animals in each group was 8-9. As shown in FIGS. 17 and 19, both intrathecal and subcutaneous injection of Compound 9 in mice can produce analgesic effects on thermal hyperalgesia in a neuralgia model induced by chronic compression of the sciatic nerve in a dose-dependent manner. The analgesic ED$_{50}$ values were 1.74 (1.38-2.20) pmol and 3.12 (2.77-3.51) mg/kg, respectively. As shown in FIGS. 18 and 20, both intrathecal and subcutaneous injection of Compound 9 in mice can produce analgesic effects on mechanical hyperalgesia in a neuralgia model induced by chronic compression of the sciatic nerve in a dose-dependent manner. The analgesic ED$_{50}$ values were 1.11 (0.63-196) pmol and 3.51 (3.28-3.74) mg/kg, respectively. It shows that compound 9 has potential application value in the treatment of neuralgia.

9. Detection of Analgesic Tolerance and Cross-Tolerance of Compound 9 and Morphine in Inflammatory Pain Induced by Complete Freund's Adjuvant (CFA)

(1) Method for Detecting Analgesia Tolerance in Inflammatory Pain Induced by CFA in Mouse CFA-induced inflammatory pain in mouse was detected by an electronic Von Frey tenderness instrument, and the basal pain threshold of normal mice was Firstly determined. Then 20 ml of CFA solution was injected subcutaneously into the mouse paw. After 4 days, the mechanical pain sensitivity value of the injected paw of the mouse was measured. And then compound 9 or morphine was injected for 6 consecutive days (lateral ventricle) or 7 consecutive days (subcutaneously), and the mice in morphine group were given compound 9 on day 7 (lateral ventricle) or day 8 (subcutaneous). The mechanical pain thresholds at different time points after administration were recorded.

(2) Data Statistics for CFA-Induced Inflammatory Pain

The experimental data were expressed as mean± standard error (Means±S.E.M.). Data for differences between groups treated with the same drug were analyzed by one-way ANOVA (Tukey HSD test of one-way ANOVA) for statistics and analysis, *P<0.05. P<0.005, *P<0.001 indicates a significant difference between the mechanical pain threshold of the drug-treated group and the pain threshold after the first day of administration. The experimental results are shown in FIGS. 21-22.

The saline group was a blank control group, and the number of animals in each group was 8-10. As shown in FIGS. 21-22, the analgesic effect for the continuous injection of morphine into the lateral ventricle or subcutaneous of the mice significantly reduced from the fourth day, resulting in analgesia tolerance. Compared with morphine, the analgesic effect of compound 9 was not significantly different from that of the first day, regardless of continuous lateral ventricle injection or subcutaneous injection of compound 9, indicating that compound 9 did not produce analgesic tolerance in CFA-induced inflammatory pain. On the seventh day (lateral ventricle) or eighth day (subcutaneous), morphine-tolerant mice administrated with compound 9 still have an analgesic effect comparable to that obtained after being administrated with compound 9 on the first day; when the mice given compound 9 for 6 consecutive days were given morphine in the lateral ventricle, they have a comparable analgesic effect as the first day. It indicates that compound 9 does not produce analgesic tolerance in CFA inflammatory pain, and there was no cross-tolerance between compound 9 and morphine. It indicates that compound 9 may still have an effective analgesic effect in patients with opioid analgesia tolerance, and has important application value in the development of alternative analgesic drugs for opioid analgesics.

10. Detection of Analgesic Tolerance and Cross-Tolerance of Compound 9 and Morphine in the Neuralgia Induced by Chronic Compression of the Sciatic Nerve (CCI).

(1) Method for Detecting Neuralgia Analgesia Tolerance Induced by CCI in Mouse

CCI-induced neuralgia in mouse was detected using a PL-200 thermal tingling instrument and an electronic Von Frey tenderness instrument. The thermal pain threshold of one group of normal mice and the mechanical pain threshold of another group of normal mice were first determined. The mice were then anesthetized with sodium pentobarbital 80 mg/kg mouse body weight) and the mice were fixed in the prone position. The right sciatic nerve was exposed and 3 mild ligation rings were made around the sciatic nerve using a 4-0 chromic catgut, 1 mm intervals. The ligation intensity is preferably a slight tremor in the right hind leg. On the 10th day after surgery, the thermal pain sensitivity value and mechanical pain sensitivity value of the right hind paw of the two groups of mice were determined. Compound 9 or morphine was then administered subcutaneously for seven consecutive days, and compound 9 was given to mice in the morphine group on day 8. The thermal tingling and mechanical pain thresholds at different time points after administration were recorded.

(2) Statistical Data of Neuralgia Induced by Chronic Compression of the Sciatic Nerve (CCI)

The experimental data were expressed as mean±standard error (Means±S.E.M.). Data for differences between groups treated with the same drug were analyzed by one-way ANOVA (Tukey HSD test of one-way ANOVA) for statistics and analysis, *P<0.05. P<0.01, *P<0.001 indicates a significant difference between the pain threshold of the drug-treated group and the pain threshold after the First day of administration. The experimental results are shown in FIGS. 23-24.

The saline group was a blank control group, and the number of animals in each group was 8. As shown in FIG. 23, from the third day, the subcutaneous continuous injection of morphine in mice has significantly reduced analgesic effect on thermal sensitivity pain induced by the chronic compression of the sciatic nerve, resulting in analgesia tolerance. Compared with morphine, the analgesic effect obtained by administering compound 9 subcutaneously for seven consecutive days was not significantly different from that obtained in the first day. On day 8, morphine-tolerant mice subcutaneously given compound 9 still have an analgesic effect comparable to that obtained by administrating compound 9 on the first day. As shown in FIG. 24, from the fourth day, the subcutaneous continuous injection of morphine in mice has significantly reduced analgesic effect on mechanical pain sensitivity induced by the chronic compression of the sciatic nerve, resulting in analgesia tolerance. Compared with morphine, the analgesic effect obtained by administering compound 9 subcutaneously for seven consecutive days was not significantly different from that obtained in the first day. On day 8, morphine-tolerant mice subcutaneously given compound 9 still have an analgesic effect comparable to that obtained by administrating compound 9 on the first day. It indicates that compound 9 does not produce analgesic tolerance in the neuralgia induced by chronic compression of the sciatic nerve. In addition, there is no cross-tolerance between compound 9 and morphine. It indicates that compound 9 may still have an effective analgesic effect in patients with opioid analgesia tolerance, and has important application value in the development of alternative analgesic drugs for opioid analgesics.

11. Detection of Regulation on Gastrointestinal Motility by Compound 9

(1) Detection Method for Gastrointestinal Movement In Vivo in Mice

Male mice of Kunming strain, weighing 26±2 g. The commonly used toner detection method was used in the detection of astrointestinal movement in vivo. The specific experimental procedure was: before the gastrointestinal movement experiment, the mice were fasted for 16 hours (free drinking during fasting), then the drug was injected through spinal cord or subcutaneously, and after 15 minutes, the activated carbon suspension prepared in advance (a physiological saline suspension containing 5% of activated carbon and 10% gum arabic) was orally perfused into the stomach in a volume of 0.1 ml per 10 g of body weight. After 30 minutes from the perfusion of activated carbon suspension, the animals were sacrificed by cervical dislocation, and then the small intestine of the animal from the pylorus to the cecum was carefully taken out. The total lengths of the small intestine from the pylorus to the cecum and the furthest distance from which the activated carbon suspension moves were measured.

(2) Statistical Data of Gastrointestinal Movement In Vivo

Gastrointestinal movement test results were evaluated by a percentage of gastrointestinal movement, and the percentage of gastrointestinal movement per mouse was calculated by dividing the moving distance of the activated carbon suspension by the total length of the small intestine. The relevant data were expressed as mean of the percentage of gastrointestinal movement±standard error (Means±S.E.M.), the data for differences between groups treated with different drug concentrations were analyzed by one-way ANOVA (Dunnett test in one-way ANOVA) for statistics and analysis, ***$P<0.001$ represented that there was a significant difference between the percentage of gastrointestinal movement of the drug-treated group and that of the saline group. The experimental results were shown in FIGS. 25-26.

In FIG. 25, the physiological saline group was a blank control group, and the drug dose of intrathecally administered compound 9 was 100, 300, and 500 pmol, and the number of mice per group was 8-9. The experimental results showed that the percentage of gastrointestinal movement in the blank solvent control group was 66.75%, and the percentages of gastrointestinal movement in the group of intrathecal injection of 100, 300 and 500 pmol of compound 9 were 45.71%, 31.40% and 21.67%, respectively. Only 300 pmol or higher will have a significant inhibitory effect on gastrointestinal movement. Therefore, compound 9 has no constipation side effects in the range of effective analgesic doses.

In FIG. 26, the physiological saline group was a blank control group, the morphine group was a positive control group, the subcutaneous administration dosage of compound 9 was 1, 10, 30 and 100 mg/kg, and the morphine dose was 10 mg/kg, and the number of mice in each group is 8. The experimental results showed that the percentage of gastrointestinal movement of the blank solvent control group was 73.97%, and the percentages of gastrointestinal movement of the groups subcutaneously injected with 1, 10, 30 and 100 mg/kg of compound 9 were 47.28%, 37.10%, 33.12% and 24.14%, respectively. The percentage of gastrointestinal movement of 10 mg/kg morphine was 16.92%. Although the inhibitory effect on gastrointestinal movement of compound 9 subcutaneous administrated was lower than that of morphine, there were still side effects of constipation in the effective analgesic dose.

11. Detection of Regulation on Cardiovascular by Compound 9

(1) Method for Detecting Blood Pressure in Rats

Wistar male rats weighing 200-250 g. After urethane (1.3 g/kg) anesthesia, the trachea was cut to prevent suffocation. The femoral was isolated and a PE-10 artery cannula was inserted in an insertion depth of approximately 2 cm. The arterial cannula was connected to a pressure transducer PT-100, and the PT-100 was connected to a biofunctional experiment BL-420F system to record mean arterial pressure and pulsatile arterial pressure. An additional PE-10 was inserted from the lumbar vertebra $L_4$-$L_5$ and inserted 3 cm along the subarachnoid space up to the spine $T_{12}$-$L_1$ for intrathecal administration. After the surgery, the rats were allowed to stabilize for 30 min. Then, intrathecal administration of physiological saline or different doses of the drug, the dose of the drug was from small to large, and each dose interval was more than 40 min. Changes in blood pressure of the rats after administration were recorded.

(2) Statistics of Regulation on Blood Pressure in Rats

The experimental results of cardiovascular regulation in rats were expressed as changes in blood pressure, and the relevant data were expressed as mean±standard error (Means±S.E.M.), Differences between groups treated with different drug concentrations were analyzed by one-way ANOVA (Bonferroni test in one-way ANOVA) for data statistics and analysis. The experimental results are shown in FIG. 27.

In FIG. 25, the physiological saline group was a blank control group, and the drug dose of the intrathecal administrated compound 9 were 1, 3, 10, and 30 nmol, and the number of rats per group was 5 (the dosage of the mouse was converted to 140, 420, 1400 and 4200 pmol based on the weight conversion table, respectively). The experiment results showed that intrathecal injection of compound 9 with a dose of more than 1 nmol produced a significant blood pressure-lowering effect than the physiological saline group. However, this dose is much greater than the analgesic dose. Thus, compound 9 does not cause side effects on the cardiovascular system over a range of effective analgesic doses.

12. Detection of Regulation on Body Temperature of Compound 9

(1) Method for Detecting Body Temperature of Mice

Mice were fixed in the manner described in Rosow et al. (1980). The ambient temperature was controlled at 21±0.5° C. and the experiment was carried out between 10 am and 2 pm. A temperature sensor attached to the biofunctional test BL-420F system was inserted into the rectum of the mouse in a depth of 2.5 cm to record the rectal temperature. The body temperatures before the intrathecal administration and at 10, 20, 30, 40, 50 and 60 minutes after administration were recorded.

(2) Statistics on Mouse Body Temperature

The experiment results of regulation on the mouse body temperature were expressed as the difference between the basal body temperature and the body temperature after administration. The relevant data were expressed as mean+standard error (Means±S.E.M.). Differences between groups treated with different drug concentrations were analyzed by one-way ANOVA (Bonfenoni test in one-way ANOVA) for data statistics and analysis. The experimental results are shown in FIG. 28.

In FIG. 28, the physiological saline group was a blank control group, and the drug doses of the intrathecal administration of compound 9 were 100, 300 and 500 pmol, and the number of mice per group was 9-14. The experiment results showed that only compound 9 intrathecally injected in a dose of 500 pmol produced a significant effect of lowering body temperature than the physiological saline group. Therefore, compound 9 has no significant regulatory effect on body temperature in the range of effective analgesic doses.

In summary, the multi-target polypeptide compounds 1-9 of the present invention have extremely strong central analgesic activity, and all of them do not produce side effects of analgesic tolerance. Compound 9 has a strong analgesic effect in different model pain such as acute thermal pain, chemical irritation pain, visceral pain, postoperative pain, inflammatory pain and neuralgia. And compound 9 does not produce constipation side effects within the effective analgesic dose range, and has no obvious regulatory effect on cardiovascular and body temperature. Therefore, compound 9 has potential application value in the preparation of analgesic drugs with high-efficiency and low-side effects.

13. Detection of Regulation on the Movement Activity of Compound 9

(1) Method for Detecting Movement Activity in Mice

The movement activity of the mice was tested by open field experiments. The experimental device is consisted of a 50×50×50 cm topless black plexiglass box and a movement monitoring system. The experiment was carried out in a soundproof environment with an indoor temperature being controlled at 22±1° C. After the experiment was started, the mice were first recorded for free movement within 30 minutes, and then compound 9 or morphine was administered subcutaneously, the movement of the mice was detected for another 150 minutes. Before the experiment for each mouse was started, the whole box was wiped with alcohol as a whole to exclude the residual odor of the previous mouse from affecting the accuracy of the data.

(2) Statistics of Movement Activity Experiments

The experimental data were expressed as mean±standard error (Means±S.E.M.), and the data for differences between groups treated with different drugs were analyzed by one-way ANOVA (Bonferroni test in one-way ANOVA) for statistics and analysis, ***P<0.001 represents that there was a significant difference between the movement activity of the drug-treated group and that of the saline group. The experimental results are shown in FIG. 29.

As shown in FIG. 29, the saline group was a blank control group, the drug dose of subcutaneous administration of compound 9 was 10 mg/kg, and the dose of morphine was also 10 mg/kg, and the number of mice per group was 8. The experimental results showed that there was no significant change in the movement activity of the mice after subcutaneous administration of 10 mg/kg of compound 9 compared with the saline group, and the total distance of movement was 71.39 m and 87.17 m, respectively. However, after subcutaneous injection of 10 mg/kg of morphine, the movement activity of the mice was significantly enhanced, with a total movement distance of 439.73 m. Thus, compound 9 has no side effects that affect movement activity over a range of effective analgesic doses.

14. Evaluation of the Addictiveness of Compound 9

The addictiveness of compound 9 was tested by conditional position preference test (CPP) and naloxone withdrawal test.

The conditional position preference experimental device is a closed device (45×20×20 cm) assembled from transparent plexiglass plates. Two 20×20×20 cm conditional preference boxes are located at both ends of the device, with a small compartment 5×20×20 cm having a passage (5×5×5 cm) connected in the middle. On the first day of the experiment, the passage was kept open, the mice was placed into the device for 15 min, and the mice that had been explored for more than 9 min in any of the preference boxes were excluded. Subsequently, continuous treatment with the drug for 3 days, during which the passage was kept closed, and compound 9 or morphine was subcutaneously administrated in every morning, then the mice were placed into a preference box for 15 minutes, and the saline was given in the afternoon, then the mice were placed into another preference box for 15 minutes. On day 5, the passage was kept opened again to ensure that the mice were free to enter into the two preference boxes, and the time that the mice stayed in the drug matching preference box within 15 minutes of the total time was recorded.

The naloxone withdrawal test is a classic test for evaluating drug addiction, and the time and dose of subcutaneous continuous administration refer to the method in Y. T. Lin et al (2015). Two hours after the last administration, 1 mg/kg of naloxone was injected subcutaneously, and the mice were immediately placed into an opaque barrel-like structure having an inner diameter of 9 cm and a height of 32 cm, and the number of jumps of the mice within 30 minutes was recorded.

(2) Data Statistics of the Addiction Evaluation Experiment

The experimental relevant data were expressed as mean±standard error (Means±S.E.M.), and the conditional position preference score represents the time spent on the drug matching preference box on day 5 of each mouse minus the time on the first day in this preference box. Differences between groups treated with different drugs in CPP trials were analyzed by one-way ANOVA (Tukey HSD test in one-way ANOVA) for data statistics and analysis. Differences in the number of jumps in naloxone withdrawal trials were analyzed using paired T test. *P<0.05, P<0.01, and *P<0.001 indicate significant differences between the drug-treated group and the saline group. The experimental results are shown in FIGS. 30-31.

The saline group was a blank control group, and the number of mice in each group was 8. As shown in FIG. 30, subcutaneous administration of compound 9 and morphine at a dose of 10 mg/kg produced significant conditional positional preference, but compound 9 at the same drug dose caused a lower degree of preference than morphine. As shown in FIG. 31, the doses administered subcutaneously at 8 hours intervals in the withdrawal test were 20, 40, 60, 80, 100, 100, and 100 mg/kg, respectively. After naloxone withdrawal, the number of jumps in mice injected with compound 9 was not significantly different from that in the saline group, with an average number of jumps of 11.63 and 1.88, respectively. The number of jumps in the morphine group was significantly increased, with an average number of jumps of 47. Thus, the addictiveness of compound 9 is reduced compared to that of the classic opioid analgesic morphine.

15. Detection of Regulation on the Movement Coordination of Compound 9

(1) Detection Method of Mice Movement Coordination

The movement coordination of the mice was detected by a ZB-200 RotaRod System. The mice were first trained for two days at a rotational speed of 16 r/min and continuously trained three times a day. The maximum movement time for each training was set to 300 s, and mice with movement time less than 180 s were excluded after the training. On day 3 of the experiment, mice were tested for movement coordination at 10, 20, 30 and 40 min after subcutaneous administration of compound 9.

(2) Data Statistics of Movement Coordination Experiments

The experimental data were expressed as mean±standard error (Means±S.E.M.), and the differences between drug treatment groups were analyzed by one-way ANOVA (Dunnett test in one-way ANOVA) for data statistics and analysis. The experimental results are shown in FIG. 32.

The saline group was a blank control group, and the number of mice in each group was 8. As shown in FIG. 32, subcutaneous administration of 10 mg/kg of compound 9 did not significantly affect movement coordination in mice. Therefore, compound 9 has no side effects that affect movement coordination at an analgesic dose.

DETAILED DESCRIPTION OF INVENTION

The method for synthesizing the multi-target polypeptide 1-9 of the present invention will now be described by way of specific examples.

Figure 1:
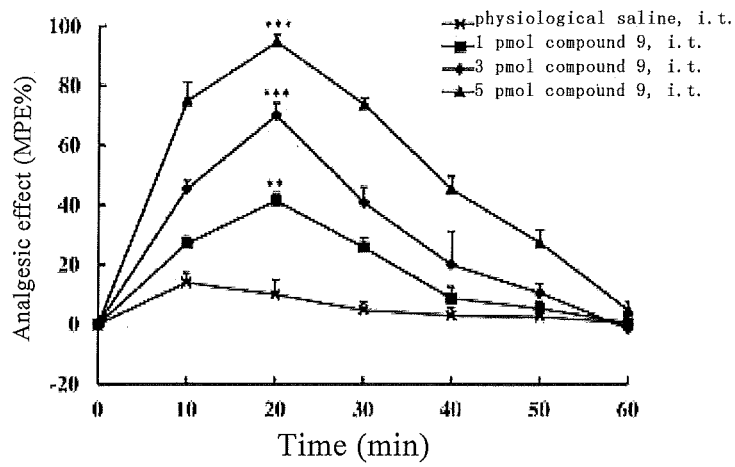
FIG. 1 is a time-effect curve of dose-dependent analgesic effect produced by intrathecal injection of compound 9 in mice.
Figure 2:
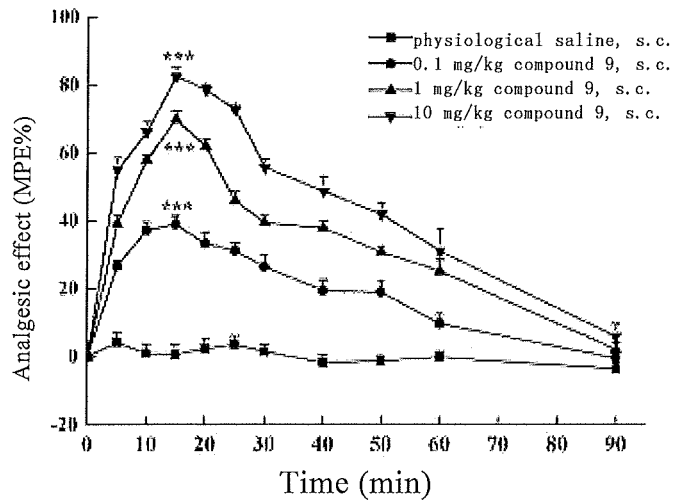
FIG. 2 is a time-effect curve of dose-dependent analgesic effect produced by subcutaneous injection of compound 9 in mice.
Figure 3:
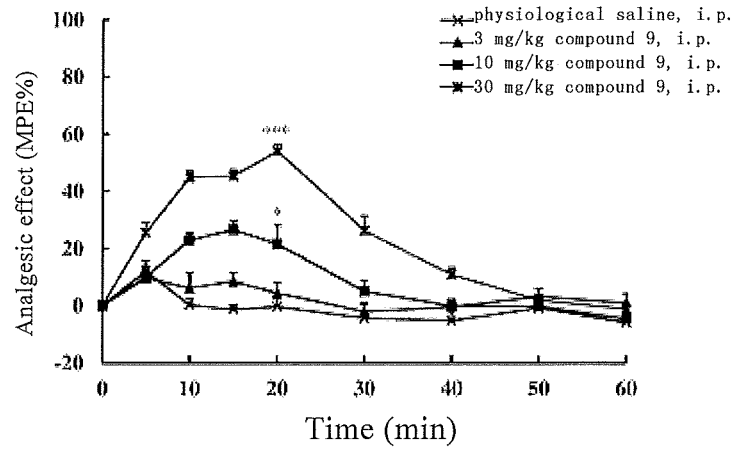
FIG. 3 is a time-effect curve of dose-dependent analgesic effect produced by intraperitoneal injection of compound 9 in mice.
Figure 4:
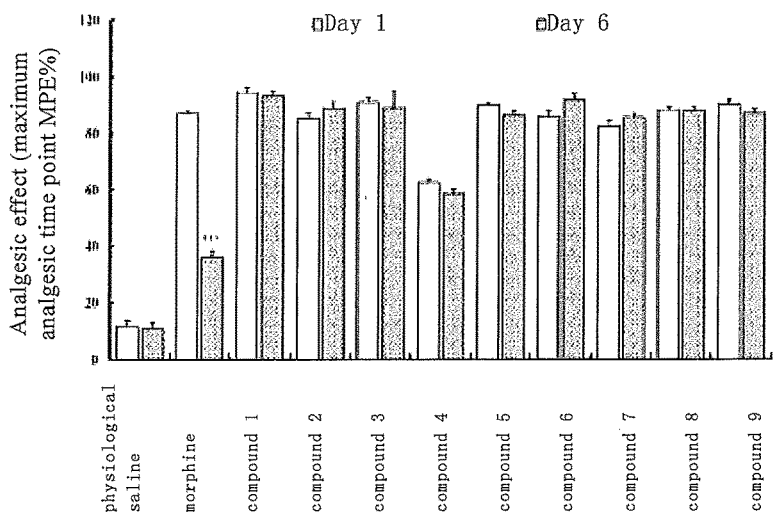
FIG. 4 is a graph showing changes in the analgesic effect caused by the injection of compounds 1-9 into the lateral ventricle of mice for six consecutive days.
Figure 5:
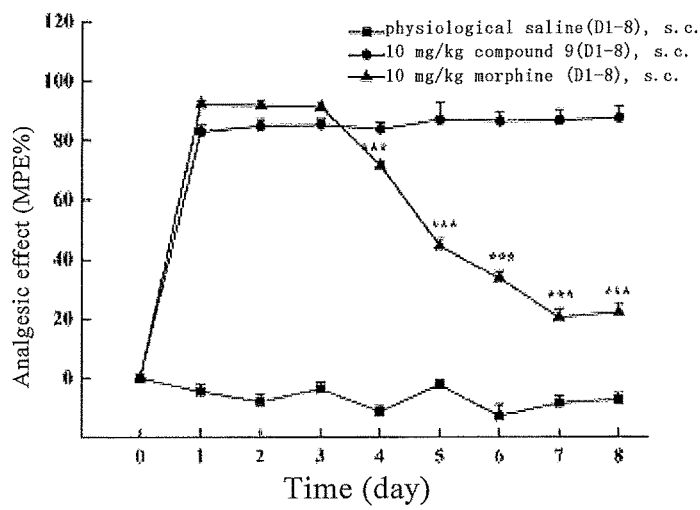
FIG. 5 is a graph showing changes in the analgesic effect caused by subcutaneous injection of compound 9 in mice for eight consecutive days.
Figure 6:
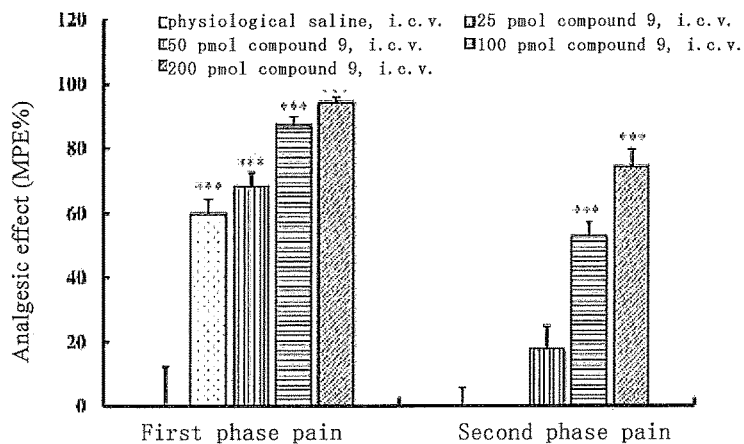
FIG. 6 is a graph showing the analgesic effect caused by injection of compound 9 into the lateral ventricle of mice in formalin-induced pain mice.
Figure 7:
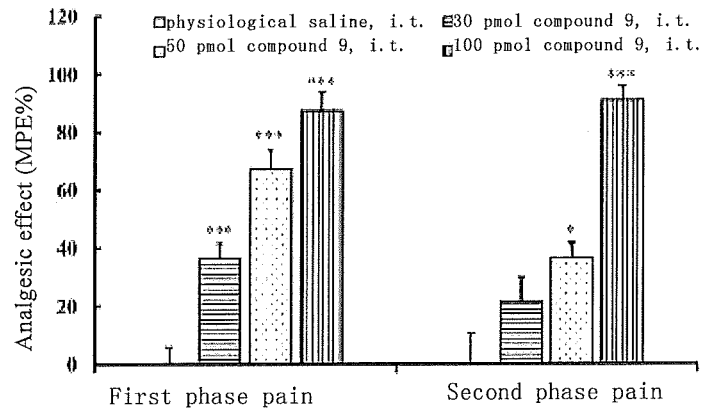
FIG. 7 is a graph showing the analgesic effect caused by intrathecal injection of compound 9 in mice in formalin-induced pain mice.
Figure 8:
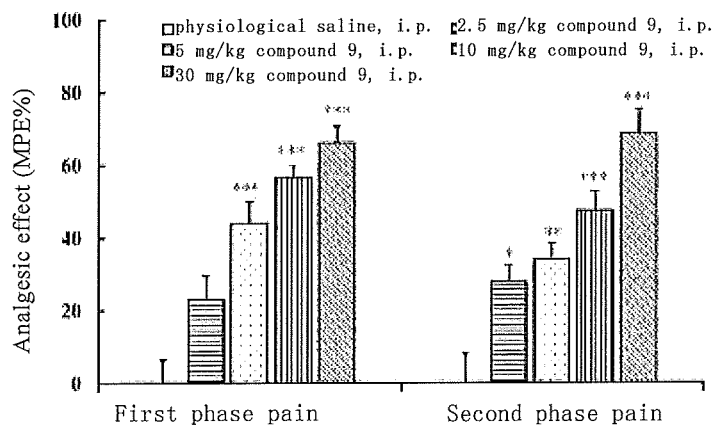
FIG. 8 is a graph showing the analgesic effect caused by intraperitoneal injection of compound 9 in mice in formalin-induced pain mice.
Figure 9:
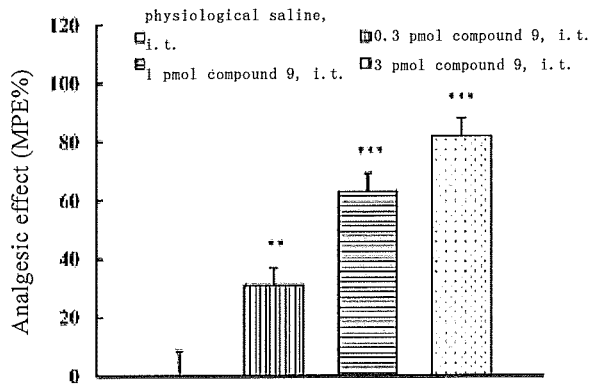
FIG. 9 is a graph showing the analgesic effect of intrathecal injection of compound 9 in mice on visceral pain induced by intraperitoneal injection of acetic acid solution.
Figure 10:
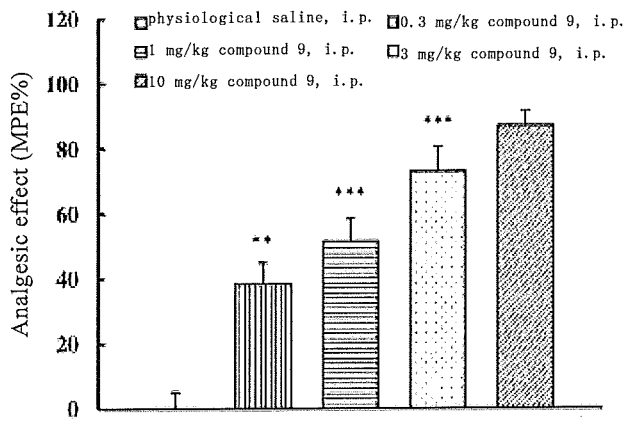
FIG. 10 is a graph showing the analgesic effect of intraperitoneal injection of compound 9 in mice on visceral pain induced by intraperitoneal injection of acetic acid solution.
Figure 11:
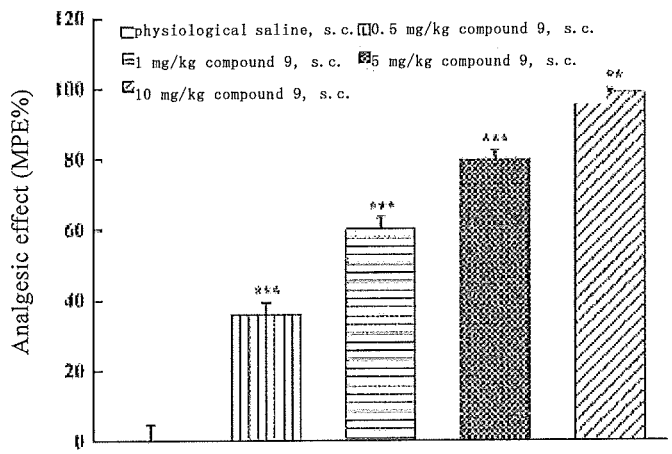
FIG. 11 is a graph showing the analgesic effect of subcutaneous injection of compound 9 in mice on visceral pain induced by intraperitoneal injection of acetic acid solution.
Figure 12:
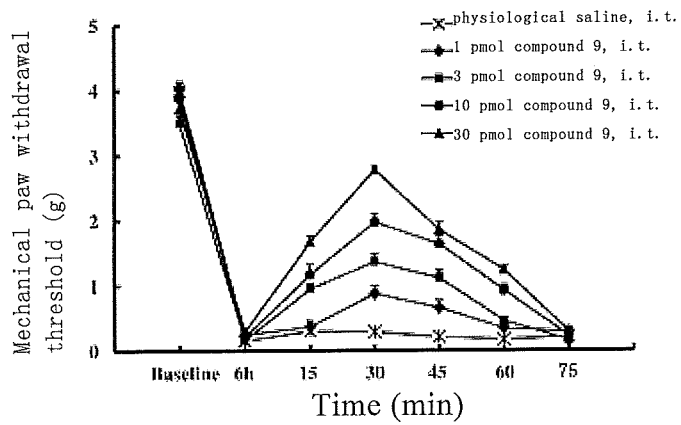
FIG. 12 is a graph showing the analgesic effect of intrathecal injection of compound 9 in mice on postoperative pain.
Figure 13:
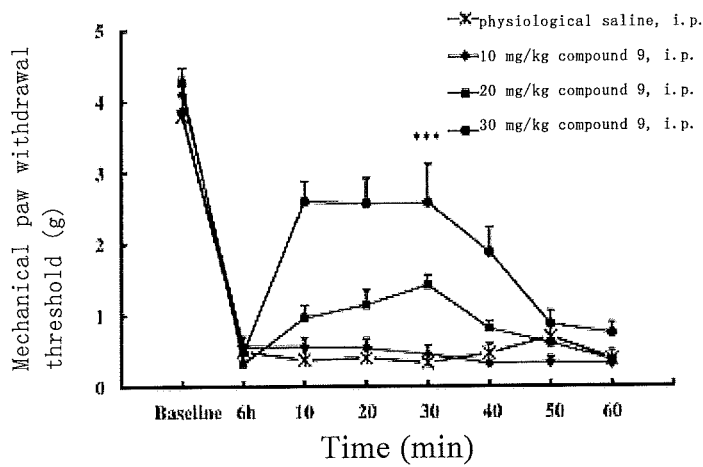
FIG. 13 is a graph showing the analgesic effect of intraperitoneal injection of compound 9 in mice on postoperative pain.
Figure 14:
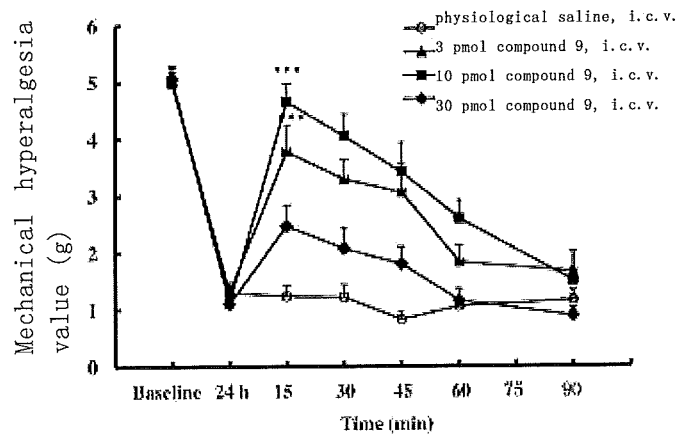
FIG. 14 is a graph showing the analgesic effect of injection of compound 9 into the lateral ventricle of mice on CFA-induced inflammatory pain.
Figure 15:
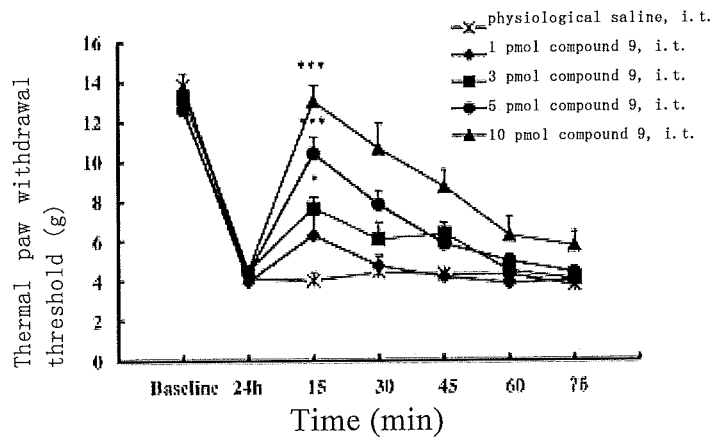
FIG. 15 is a graph showing the analgesic effect of intrathecal injection of compound 9 in mice on inflammatory pain induced by carrageenan polysaccharides.
Figure 16:
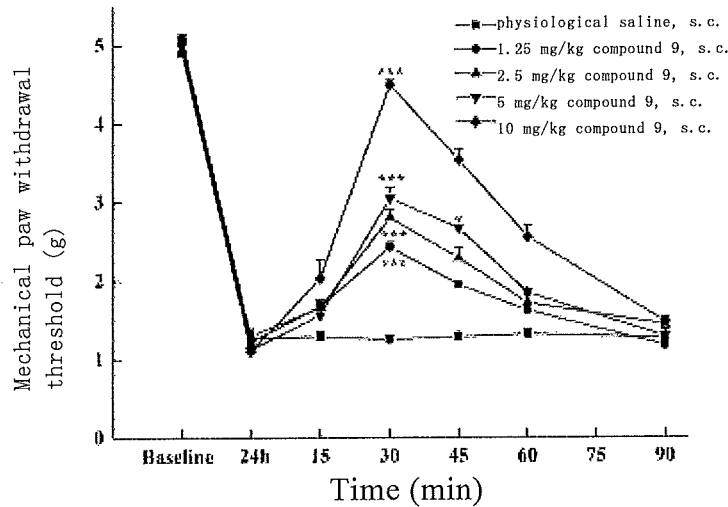
FIG. 16 is a graph showing the analgesic effect of subcutaneous injection of compound 9 in mice on inflammatory pain induced by carrageenan polysaccharide.
Figure 17:
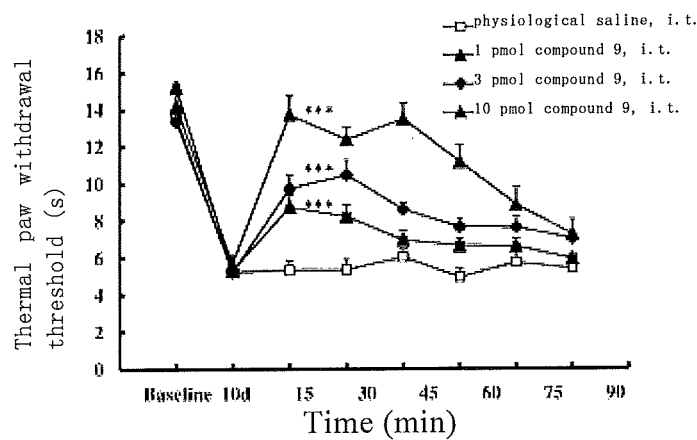
FIG. 17 is a graph showing the analgesic effect of intrathecal injection of compound 9 in mice on thermal pain in a neuralgia CCI model.
Figure 18:
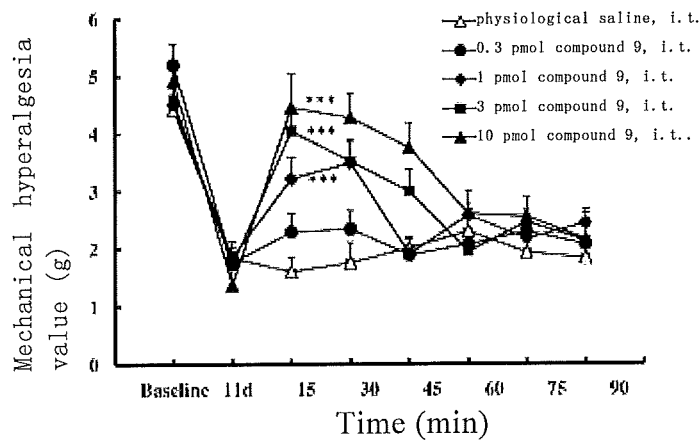
FIG. 18 is a graph showing the analgesic effect of intrathecal injection of compound 9 in mice on mechanical pain in a neuralgia CCI model.
Figure 19:
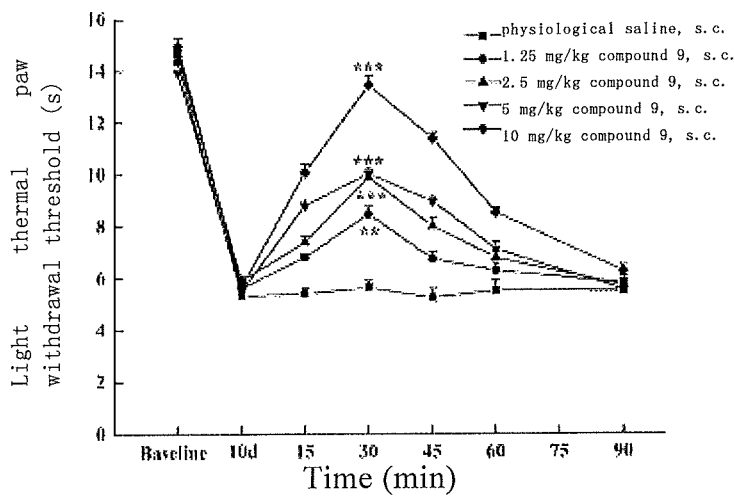
FIG. 19 is a graph showing the analgesic effect of subcutaneous injection of compound 9 in mice on thermal pain in a neuralgia CCI model.
Figure 20:
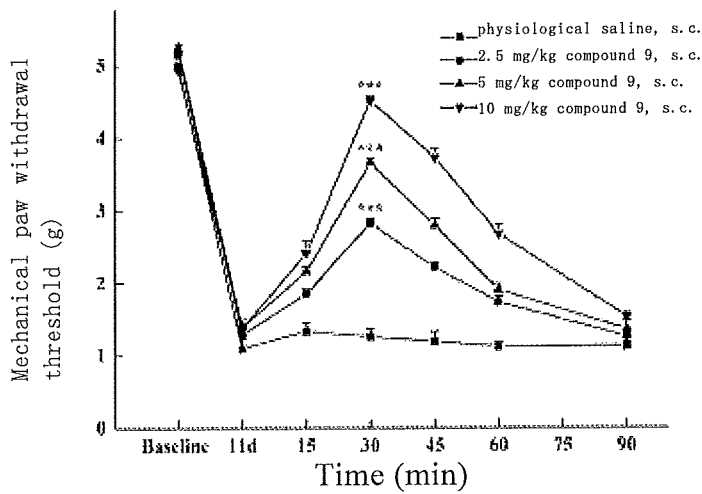
FIG. 20 is a graph showing the analgesic effect of subcutaneous injection of compound 9 in mice on mechanical pain in a neuralgia CCI model.
Figure 21:
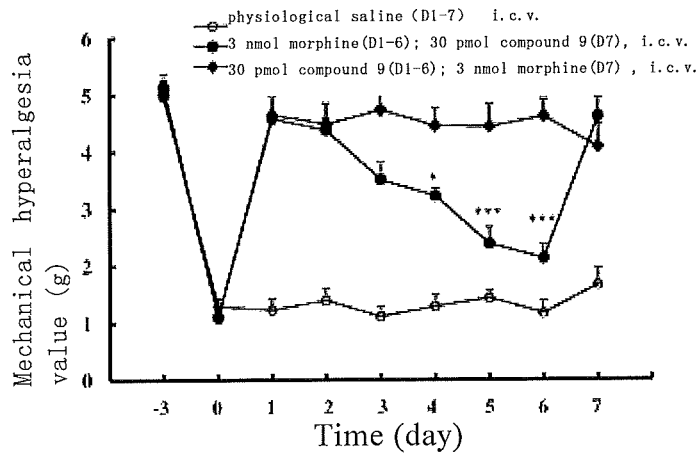
FIG. 21 is a graph showing the analgesic tolerance and cross-tolerance of compound 9 and morphine injected into the lateral ventricle of mice in CFA-induced inflammatory pain.
Figure 22:
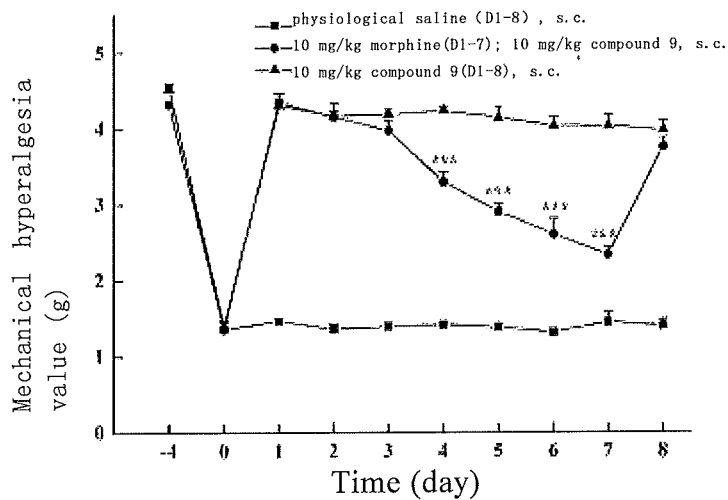
FIG. 22 is a graph showing the analgesic tolerance and cross-tolerance of subcutaneous injection of compound 9 and morphine in mice in CFA-induced inflammatory pain.
Figure 23:
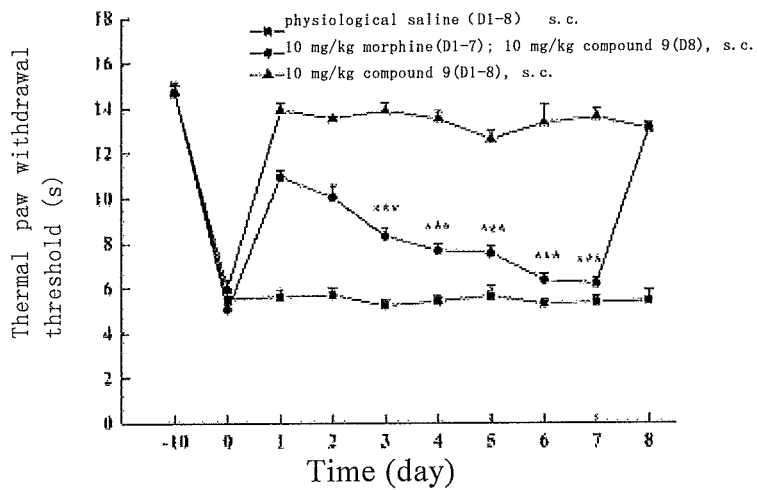
FIG. 23 is a graph showing the analgesic tolerance and cross-tolerance of subcutaneous injection of compound 9 and morphine in mice on thermal pain in a neuralgia CCI model.
Figure 24:
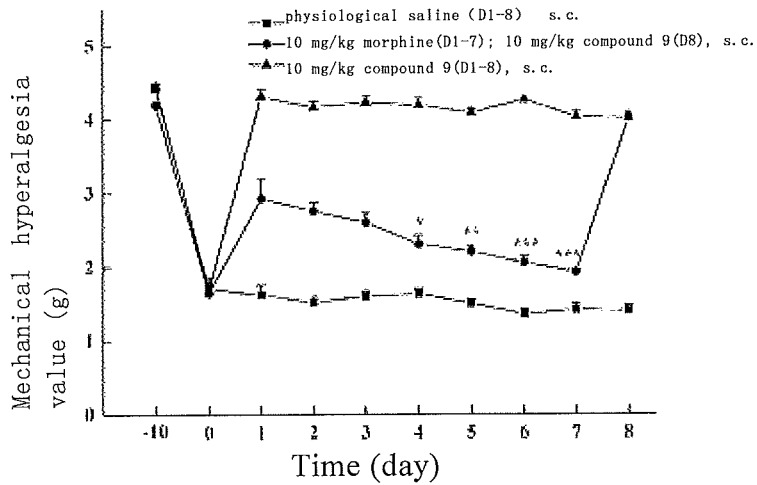
FIG. 24 is a graph showing the analgesic tolerance and cross-tolerance of subcutaneous injection of compound 9 and morphine in mice on mechanical pain in a neuralgia CCI model.
Figure 25:
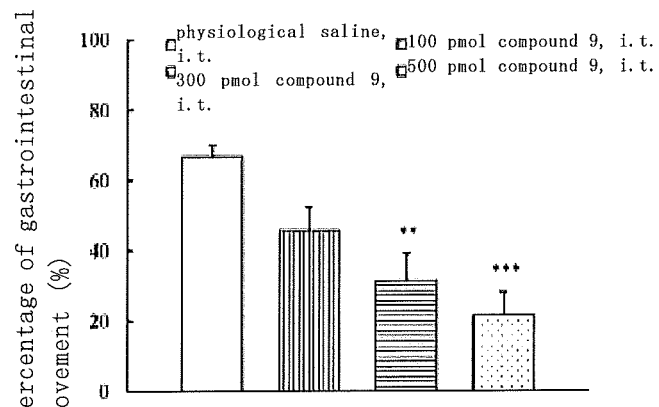
FIG. 25 is a graph showing the effect of intrathecal injection of compound 9 in mice on gastrointestinal motility.
Figure 26:
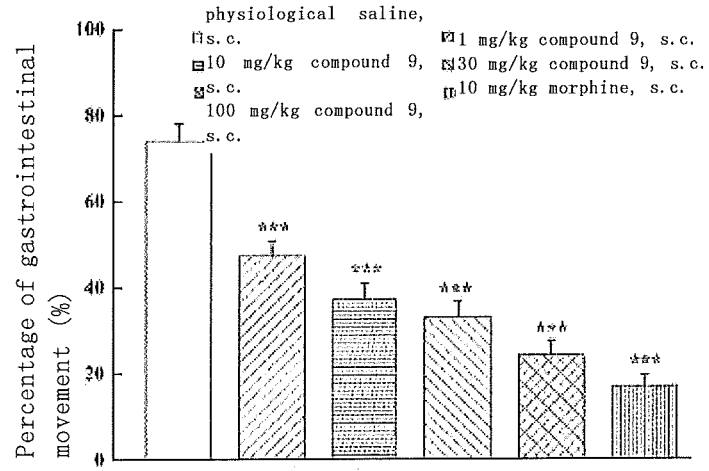
FIG. 26 is a graph showing the effect of subcutaneous injection of compound 9 in mice on gastrointestinal motility.
Figure 27:
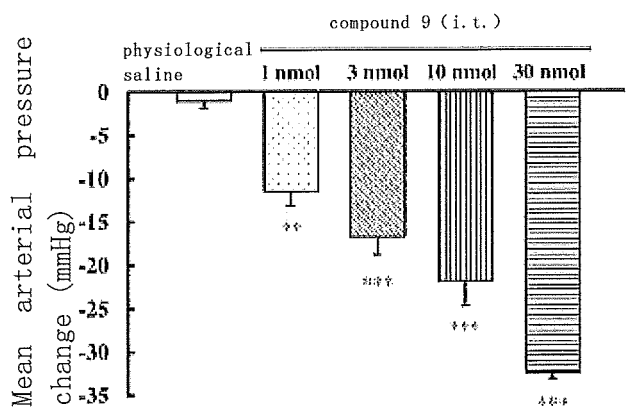
FIG. 27 is a graph showing the modulation effect of intrathecal injection of compound 9 in mice on the cardiovascular system.
Figure 28:
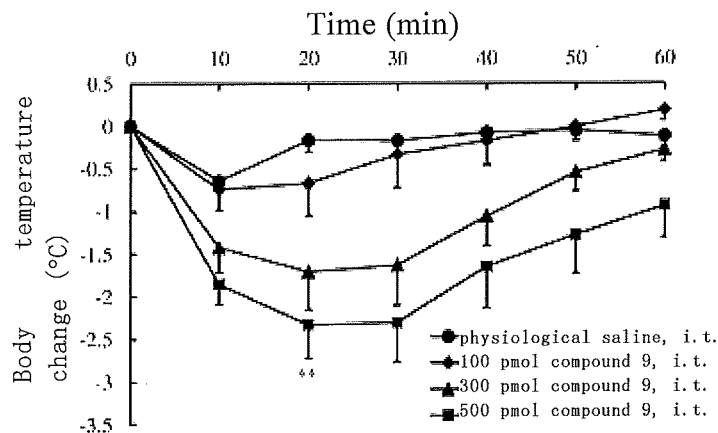
FIG. 28 is a graph showing the modulation effect of intrathecal injection of compound 9 in mice on a body temperature regulatory system.
Figure 29:
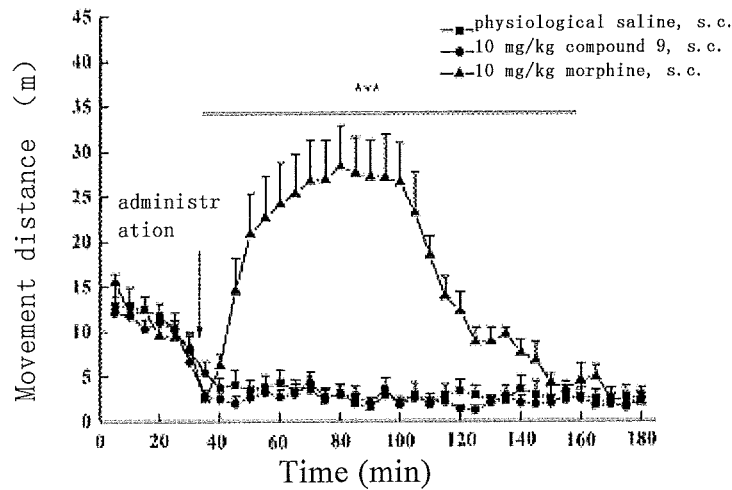
FIG. 29 is a graph showing the modulation effect of subcutaneous injection of compound 9 in mice on movement activity.
Figure 30:
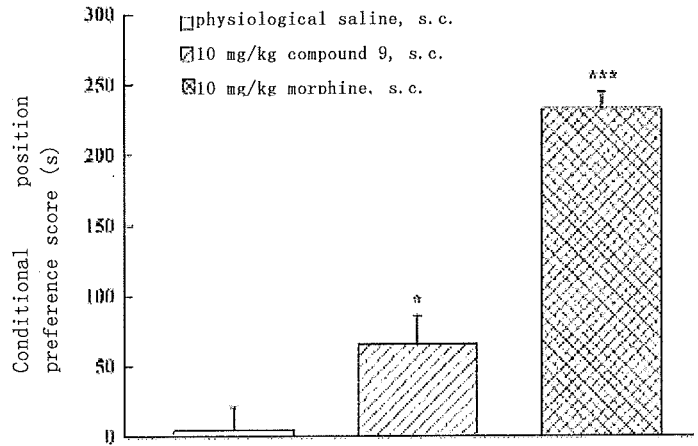
FIG. 30 is a graph showing the modulation effect of subcutaneous injection of compound 9 in mice on the conditional position.
Figure 31:
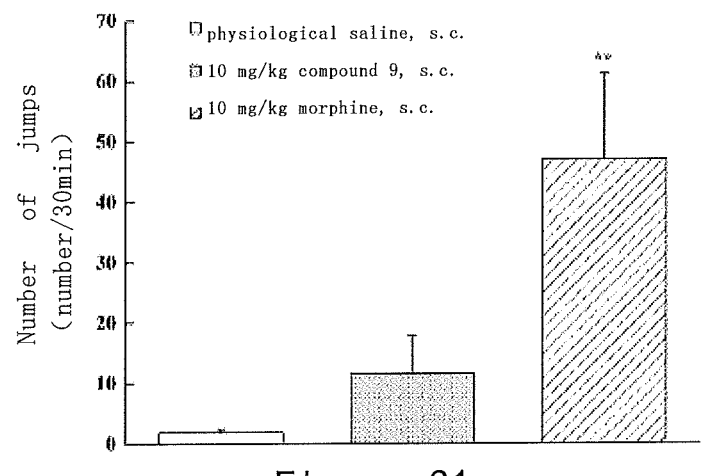
FIG. 31 is a graph showing the response of subcutaneous injection of compound 9 in mice to naloxone withdrawal.
Figure 32:
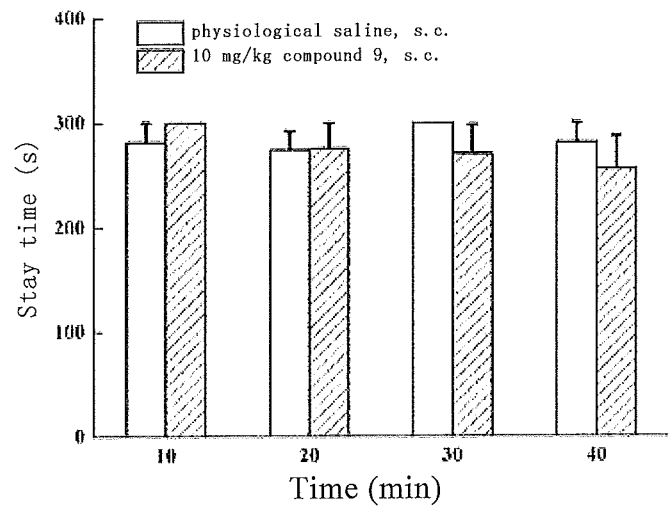
FIG. 32 is a graph showing the regulation effect of movement coordination of subcutaneous injection of compound 9 in mice.

Apparatus: High Performance Liquid Chromatograph (HPLC) was a Delta 600 from Waters; analytical column: XBridge™ BEH 130 Prep $C_{18}$, 4.6 mm×250 mm; preparative column: XBridge™ BEH 130 Prep $C_{18}$, 19 mm×250 mm. The mass spectrometer was Mariner ESI-TOF MS, Applied Biosystems, CA. Manual solid phase peptide synthesizer, designed by the present laboratory and made by glassworker (the design principle of the synthesizer is specifically referred to FIG. 4 on page 14 in "Fmoc solid phase peptide synthesis" edited by Chen W C and White P D, and based on it, partial improvement was made to replace the nitrogen gas method with mechanical stirring to achieve the purpose of thorough mixing of the reaction solution). Reagent: Resin was Rink-Amide-MBNA-Resin (1% DVB, 200-400 mesh, substitution value S=0.43 mol/g resin), purchased from Tianjin Nankai Hecheng Company. N-α-Fmoc protected amino acids (Fmoc-Aa/Boc-Aa), N-hydroxy benzotriazole (HOBt), O-benzotriazole-N,N,N',N'-tetramethyl-urea-hexafluorophosphate (HBTU), diisopropylethylamine (DIEA) and triisopropylsilane (TIS) were purchased from GL Biochem(Shanghai) Ltd. Ninhydrin is a product of Shanghai Reagent Third Factory. Dichloromethane (DCM), N,N-dimethylformamide (DMF), hexahydropyridine (piperidine), methanol (MeOH) and pyridine were purchased from Tianjin Second Reagent Factory, trifluoroacetic acid (TFA), phenol and pyridine were products of Tianjin Reagent First Factory; the above organic reagents are re-steamed before use.

Example 1

Synthesis of Compound 1

(1) Resin pretreatment: 600 mg of Rink-Amide-MBHA resin having a substitution value of 043 mmol/g was weighed and added into a synthesizer, and DCM was added and then stirred for 30 min. The resin was sufficiently swollen, and the solvent was removed under reduced pressure.

(2) Removal of Fmoc group protection: in the swollen resin, in which the solvent was removed, a mixed solution of hexahydropyridine, DBU and DMF was added (the volume ratio of the three is 1:1:98), stirred for 5 minutes and then suction-filtered, repeated for 3 times, and suction-filtered. DMF was finally added, stirred for 3 min, and suction-filtered, and repeated for 4 times to obtain a resin sample unprotected by Fmoc group.

(3) Indene detection: the following was added into test tube in the following order: resin sample, 0.1 ml reagent 1̂, 0.2 ml reagent 2̂, 0.1 ml reagent 3̂, incubated in a boiling water bath for 3-10 min and observed. Both of the solution and the resin were blue, which indicates that the Fmoc protecting group was completely removed. The three reagents used for the indene detection were: reagent 1̂ 80 g phenol/20 ml ethanol; reagent 2̂ 2.0 ml 0.001 M potassium cyanide (water)/98 ml pyridine; reagent 3̂ 5 g ninhydrin/100 ml ethanol.

(4) Condensation of amino acids: N-α-Fmoc protected Fmoc-Phe-OH, N-hydroxy benzotriazole, O-benzotriazole-N,N,N',N'-tetramethylurea-hexafluorophosphate were completely dissolved in DMF in a molar ratio of 1:1:1, and then twice molar amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min. and the solvent was evaporated. DME was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH. Fmco-Gln(Trt)-OH, Fmoc-Pro-OH, Fmoc-Gln(Trt)-OH, Fmoc-Phe-OH, Fmoc-Gly-OH, Fmoc-D-Ala-OH and Fmoc-NMe-Tyr(tBu)—OH to obtain peptide resin NMe-Tyr(tBu)-D-Ala-Gly-Phe-Gln (Trt)-Pro-Gln(Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin NMe-Tyr(tBu)-D-Ala-Gly-Phe-Gln(Trt)-Pro-Gln(Trt)-Arg(Pbf)-Phe-Resin was placed in the reactor and the cleavage agent (it was prepared by mixing TEA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C. and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 201.6 mg of a white crude peptide solid powder, yield 69.4%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by a UV detector, freeze-dried, and the above-mentioned desalted peptide compound was separated and purified by reverse phase high performance liquid chromatography (HPLC) CIS column (XBridge™ BEH 130Prep C18, 19 mm×250 mm), and the sample main peak was collected after separation. Purified compound 1 sample having a purity of 99.5% and a total yield of 22.81% was obtained. The results of mass spectrometty and chromatographic analysis are shown in Table 2.

Example 2

Synthesis of Compound 2

(1) Resin pretreatment: 600 mg Rink-Amide-MBHA resin having a substitution value of 0.43 mmol/g was weighed and added into a synthesizer, and DCM was added and stirred for 30 min. The resin was sufficiently swollen, and the solvent was removed under reduced pressure.

(2) Removal of Fmoc group protection: same as example 1.

(3) Indene detection: same as example 1.

(4) Condensation of amino acids: N-α-Fmoc protected Fmoc-Phe-OH, N-hydroxy benzotriazole, O-benzotriole-N, N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected. by Fmoc group obtained in the step (2) (the molar ratio of the Fmoc-Phe-OH to the resin unprotected by Fmoc group is 1:2.5) were added into the synthesizer, the reaction was stirred under argon for 60 min. and the solvent was evaporated. DMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-Gln(Trt)-OH, Fmoc-NMe-Phe-OH, Fmoc-Gly-OH, Fmoc-D-Ala-OH and Fmoc-Tyr (tBu)-OH to obtain peptide resin Tyr(tBu)-D-Ala-Gly-NMe-Phe-Gln(Trt)-Pro-Gln (Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TEA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-NMe-Phe-Gln(Trt)-Pro-Gln(Trt)-Arg(Pbf)-Phe-Resin was placed in the reactor and the cleavage agent (it was prepared by mixing TEA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 273.1 mg of a white crude peptide solid powder, yield 81.0%.

(7) Desalting and purification: all the crude product was dissolved in 20% acetic acid solution in batches, and the solution was passed through a Sephadex G25 Sephadex column (2.0/25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 2 sample having a purity of 95.65% and a total yield of 10.8% was obtained. The results of mass spectrometry and chromatographic analysis are shown in Table 2.

Example 3

Synthesis of Compound 3

(1) Resin pretreatment: 600 mg of Rink-Amide-MBHA resin having a substitution value of 0.5 mmol/g was weighed and added into a synthesizer, and further stirred for 30 min after adding DCM, the resin was sufficiently swollen, and the solvent was drained under reduced pressure.

(2) Removal of Fmoc group protection: same as example 1, (3) Indene detection: same as example 1.

(4) Condensation of amino acids: N-α-Fmoc protected Fmoc-Phe-OH, N-hydroxy benzotriazole, O-benzotriazole-N,N,N',N'-tetramethylurea-hexafluorophosphate were completely dissolved in DMF in a molar ratio of 1:1:1, and then twice molar amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min. and the solvent was evaporated. DME was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-Gly-OH, Fmoc-Phe-OH, Fmoc-Gly-OH, Fmoc-D-Ala-OH and Fmoc-Tyr(tBu)-OH to obtain peptide resin Tyr(tBu)-D-Ala-Gly-Phe-Gly-Pro-Gln(Trt)-Arg(Pbf)-Phe-Resin.

(6) Cleavage of the peptide chain of compound 3 from the resin: after all the amino acid residues of the peptide chain were completely condensed, tBu, Trt and Pbf protecting groups can be removed under the acidic condition by the cleavage agent TEA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-Phe-Gly-Pro-Gln(Trt)-Arg(Pbf)-Phe-Resin was placed in the reactor and the cleavage agent (it was prepared by mixing TFA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 297.9 mg of a white crude peptide solid powder, yield 95.5%.

(7) Desalting and Purification of compound 3: all the crude product was dissolved in 20% acetic acid solution in hatches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 3 sample having a purity of 96.06% and a total yield of 16.06% was obtained. The results of mass spectrometry and chromatographic analysis are shown in Table 2.

Example 4

Synthesis of Compound 4

(1) Resin pretreatment: 600 mg of Rink-Amide-MBHA resin having a substitution value of 0.43 mmol/g was weighed and added into a synthesizer, and DCM was added and then stirred for 30 min. The resin was sufficiently swollen, and the solvent was removed under reduced pressure.

(2) Removal of Fmoc group protection: same as example 1.

(3) Indene detection: same as example 1.

(4) Condensation of amino acids: N-α-Fmoc protected Fmoc-Phe-OH, N-hydroxybenzotriazole, O-benzotriazole-N,N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. DMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-Leu-OH, Fmoc-Phe-OH, Fmoc-Gly-OH, Fmoc-D-Ala-OH and Fmoc-Tyr(iBu)-OH to obtain peptide resin Tyr(tBu)-D-Ala-Phe-Leu-Pro-Gln(Trt)-Arg(Pbf)-Phe-Resin.

(6) Cleavage of the peptide chain from the resin: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times. MeOH 3 min×1 time: DCM 3 min×1 time, MeOH 3 min×2. The stir bar was removed, the synthesizer was sealed (gel plug), and suction-filtered thoroughly (at least 2 hours). The dried peptide resin Tyr(tBu) D-Ala-Gly-Phe-Leu-Pro-Arg(Pbf)-Phe-Resin was placed in the reactor and the cleavage agent (it was prepared by mixing TFA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 181.5 mg of a white crude peptide solid powder, yield 64.2%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 4 sample having a purity of 99.15% and a total yield of 38.6% was obtained. The results of mass spectrometry and chromatographic analysis are shown in Table 2.

Example 5

Synthesis of Compound 5

(1) Resin pretreatment: 600 mg of Rink-Amide-MBHA resin having a substitution value of 0.5 mmol/g was weighed and added into a synthesizer, and further stirred for 30 min after adding DCM, the resin was sufficiently swollen, and the solvent was drained under reduced pressure.

(2) Removal of Fmoc group protection: same as example 1.

(3) Indene detection: same as example 1.

(4) Condensation of amino acids: N-α-Fmoc protected Fmoc-Phe-OH, N-hydroxybenzotriazole, O-benzotriazole-N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. DMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both if the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-Met-OH, Fmoc-Phe-OH, Fmoc-Gly-OH, Fmoc-D-Ala-OH and Fmoc-Tyr(tBu)-OH to obtain peptide resin Tyr(tBu)-D-Ala-Gly-Phe-Met-Pro-Gln(Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-Phe-Met-Pro-Gln(Trt)-Arg(Pbf)-Phe-Resin was placed in the reactor and the cleavage agent (it was prepared by mixing TFA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain a white crude peptide solid powder. The crude peptide powder of compound 5 was 311.8 mg, and the yield was 93.3%, (7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 5 sample having a purity of 99.33% and a total yield of 54.39% was obtained. The results of mass spectrometry and chromatographic analysis are shown in Table 2.

Example 6

Synthesis of Compound 6

(1) Resin pretreatment: 600 mg of Rink-Amide-MBHA resin having a substitution value of 0.43 mmol/g was weighed and added into a synthesizer, and DCM was added and then stirred for 30 min. The resin was sufficiently swollen, and the solvent was removed under reduced pressure.

(2) Removal of Fmoc group protection: same as example 1.

(3) Indene detection: same as example 1.

(4) Condensation of amino acids: N-α-Fmoc protected Fmoc-Phe-OH, N-hydroxybenzotriazole, O-benzotriazole-N,N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. DMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln (Trt)-OH, Fmoc-Pro-OH, Fmoc-D-Met-Fmoc-Phe-OH, Fmoc-Gly-OH, Fmoc-D-Ala-OH and Fmoc-Tyr(tBu)-OH to obtain peptide resin Tyr(tBu)-D-Ala-Gly-Phe-D-Met-Pro-Gln(Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-Phe-D-Met-Pro-Gln(Trt)-Arg(Pbf)-Phe-Resin was placed in the reactor and the cleavage agent (it was prepared by mixing TFA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 165.9 mg of a white crude peptide solid powder, yield 57.7%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation, Purified compound 6 sample having a purity of 99.18% and a total yield of 28.62% was obtained. The results of mass spectrometry and chromatographic analysis are shown in Table 2.

Example 7

Synthesis of Compound 7

(1) Resin pretreatment: 600 mg of Rink-Amide-MBHA resin having a substitution value of 0.43 mmol/g was weighed and added into a synthesizer, and DCM was added and then stirred for 30 min. The resin was sufficiently swollen, and the solvent was removed under reduced pressure.

(2) Removal of Fmoc group protection: same as example 1.

(3) Indene detection: same as example 1.

(4) Condensation of amino acids: N-α-Fmoc protected Fmoc-Phe-OH. N-hydroxybenzotriazole, O-benzotriazole-N,N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. DMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-D-Leu-OH, Fmoc-Phe-OH, Fmoc-Gly-OH, Fmoc-D-Ala-OH and Fmoc-Tyr(tBu)-OH to obtain peptide resin Tyr(tBu)-D-Ala-Gly-Phe-D-Leu-Pro-Gln(Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-Phe-D-Leu-Pro-Gln(Trt)-Arg(Pbf)-Phe-Resin was placed in the reactor and the cleavage agent (it was prepared by mixing TFA:TIS:water in a volume ratio of 95:2.5:2.5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 172.6 mg of a white crude peptide solid powder, yield 61.1%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) $C_{18}$ column (XBridge™ BEH 130Prep $C_{18}$, 19 mm×250 mm), and the sample main peak was collected after separation. Purified compound 7 sample having a purity of 99.79% and a total yield of 33.48% was obtained. The results of mass spectrometry and chromatographic analysis are shown in Table 2.

Example 8

Synthesis of Compound 8

(1) Resin pretreatment: 600 mg of Rink-Amide-MBHA resin having a substitution value of 0.43 mmol/g was weighed and added into a synthesizer, and DCM was added and then stirred for 30 min. The resin was sufficiently swollen, and the solvent was removed under reduced pressure.

(2) Removal of Fmoc group protection: same as example 1.

(3) Indene detection: same as example 1.

(4) Condensation of amino acids: N-α-Fmoc protected Fmoc-Phe-OH, N-hydroxy benzotriazole, O-benzotriazole-N,N,N',N'-tetramethylurea-hexafluorophosphate were completely dissolved in DMF in a molar ratio of 1:1:1, and then twice amount of diisopropylethylamine (DIEA) relative to Fmoc-Phe-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. IMF was added, stirred for 3 min, then suction-filtered, and repeated for 3 times to obtain a sample of the peptide resin; according to the step (3), the indene detection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-D-Ala-OH, Fmoc-Phe-OH, Fmoc-Gly-OH, Fmoc-D-Ala-OH and Fmoc-Tyr(tBu)-OH to obtain peptide resin Tyr(tBu)-D-Ala-Gly-Phe-D-Ala-Pro-Gln(Trt)-Arg(Pbf)-Phe-Resin.

(6) Cleavage of the peptide chain: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times, MeOH 3 min×1 time; DCM 3 min×1 time, MeOH 3 min×2. The stir bar was removed, the synthesizer was sealed (gel plug), and suction-filtered thoroughly (at least 2 hours). The dried peptide resin Tyr(tBu)-D-Ala-Gly-Phe-D-Ala-Pro-Gln(Trt)-Arg(Pbf)-Phe-Resin was placed in the reactor and the cleavage agent (it was prepared by mixing TFA:TIS:water in a volume ratio of 95:2,5:2,5, adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 177.4 mg of a white crude peptide solid powder, yield 65.2%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%. The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 8 sample having a purity of 98.78% and a total yield of 35.36% was obtained. The results of mass spectrometry and chromatographic analysis are shown in Table 2.

Example 9

Synthesis of Compound 9

(1) Resin pretreatment: 600 mg of Rink-Amide-MBHA resin having a substitution value of 0.5 mmol/g was weighed and added into a synthesizer, and DCM was added and then stirred for 30 min. The resin was sufficiently swollen, and the solvent was removed under reduced pressure.

(2) Removal of Fmoc group protection: same as example 1.

(3) Indene detection: same as example 1, (4) Condensation of amino acids: N-α-Fmoc protected Fmoc-Phe-OH, N-hydroxy benzotriazole, O-benzotriazole-N,N,N',N'-tetramethylurea-hexafluorophosphate were completely dissolved in DMF in a molar ratio of 1:1:1, and then twice amount of diisopropylethylamine (DIEA) relative to Fmoc-Ala-OH was added, and then mixed thoroughly to obtain a mixed solution; the mixed solution and the resin unprotected by Fmoc group obtained in the step (2) (the molar ratio of the Fmoc-Phe-OH to the resin unprotected by Fmoc group is 1:2.5) were added into the synthesizer, the reaction was stirred under argon for 60 min and the solvent was evaporated. DMF was added, stirred for 3 min, then suction-filtered, and repeated for 3 times to obtain a sample of the peptide resin; according to the step (3), the indene inspection was carried out, the indene detection solution was light yellow, and the resin was colorless, which indicate complete condensation. The Fmoc protecting group was removed according to the step (2), and then indene detection was performed according to the step (3). Both of the solution and the resin were blue, which indicates that the Fmoc protecting group was completely removed, and the peptide resin unprotected by Fmoc group was obtained.

(5) Extension of the peptide chain: the peptide resin unprotected by Fmoc group obtained in the step (4) was sequentially subjected to the process of the step (4) to complete condensation of Fmoc-Arg(Pbf)-OH, Fmoc-Gln(Trt)-OH, Fmoc-Pro-OH, Fmoc-Gly-OH, Fmoc-NMe-Phe-OH, Fmoc-Gly-OH, Fmoc-D-Ala-OH and Fmoc-Tyr(tBu)-OH to obtain peptide resin Tyr(tBu)-D-Ala-Gly-NMe-Phe-Gly-Pro-Gln(Trt)-Arg(Pbf)-Ala-Resin.

(6) Cleavage of the peptide chain from the resin: after all the amino acid residues of the peptide chain were completely condensed, tBu, Trt and Pbf protecting groups can be removed under the acidic condition by the cleavage agent TFA, and therefore, the cleavage is directly performed without removing protecting groups. The resin was alternately washed according to the following operations: DCM 3 min×2 times. MeOH 3 min×1 time, DCM 3 min×1 time. MeOH 3 min×2. The stir bar was removed, the synthesizer was sealed (gel plug), and suction-filtered thoroughly (at least 2 hours). The dried peptide resin Tyr(tBu)-D-Ala-Gly-NMe-Phe-Gly-Pro-Gln(Trt)-Arg(Pbf)-Ala-Resin was placed in the reactor and the cleavage agent (it was prepared by mixing TFA:TIS:water in a volume ratio of 95:2.5:2.5. adding 18 ml of cleavage agent per gram of peptide resin) was added, and subjected to cleavage reaction at room temperature for 2.5 hours (stirred once every 15 minutes for 1 minute). After filtration, the filtrate was sufficiently dried under reduced pressure at a temperature not higher than 37° C., and then precipitated with diethyl ether at not higher than −10° C., and shaken to allow the crude peptide to be precipitated as a white precipitate. After standing, the supernatant was aspirated, water was added to dissolve the precipitate, and the diethyl ether was separated from the aqueous phase by a separating funnel. The aqueous phases were combined, freeze-dried to obtain 308.5 mg of a white crude peptide solid powder, yield 97.51%.

(7) Desalting and purification of crude peptide; all the crude product was dissolved in 20% acetic acid solution in batches, and the solution was passed through a Sephadex G25 Sephadex column (2.0×25 cm), and the mobile phase was acetic acid solution having a volume concentration of 20%, The main peak was collected by an ultraviolet detector and then freeze-dried. The above-mentioned desalted peptide compound was separated and purified by reverse phase high performance liquid chromatography (HPLC) C18 column (XBridge™ BEH 130Prep C18, 19 mm×250 mm), and the sample main peak was collected after separation. Purified compound 9 sample having a purity of 97.49% and a total yield of 32.28% was obtained. The results of mass spectrometry and chromatographic analysis are shown in Table 2.

The invention claimed is:

1. A multi-target polypeptide of opioid and neuropeptide FF receptors, consisting of a sequence selected from the group consisting of:

```
                                         (SEQ ID NO: 4)
Tyr-D-Ala-Gly-Phe-Gly-Pro-Gln-Arg-Phe-NH2, (SEQ ID NO: 5)
Tyr-D-Ala-Gly-Phe-Leu-Pro-Gln-Arg-Phe-NH2, (SEQ ID NO: 6)
Tyr-D-Ala-Gly-Phe-Met-Pro-Gln-Arg-Phe-NH2, (SEQ ID NO: 7)
Tyr-D-Ala-Gly-Phe-D-Met-Pro-Gln-Arg-Phe-NH2, (SEQ ID NO: 8)
Tyr-D-Ala-Gly-Phe-D-Leu-Pro-Gln-Arg-Phe-NH2, (SEQ ID NO: 9)
Tyr-D-Ala-Gly-Phe-D-Ala-Pro-Gln-Arg-Phe-NH2, and (SEQ ID NO: 10)
Tyr-D-Ala-Gly-NMe-Phe-Gly-Pro-Gln-Arg-Phe-NH2.
```

2. A method for synthesizing the multi-target polypeptide of opioid and neuropeptide FF receptors according to claim 1, comprising:

(a) resin pretreatment: a Rink-Amide-MBHA resin is stirred in dichloromethane, the resin is fully swelled, and the solvent is evaporated under reduced pressure followed by addition of DMF for washing to obtain a swelled resin;

(b) removal of Fmoc group protection: in the swelled resin a mixed solution of hexahydropyridine, 1,8-diazabicycloundecyl-7-ene and DMF is added at a volume ratio of 1:1:98, stirred for 5 minutes, then evaporated, repeated 3 times followed by addition of DMF for washing and indene detection to obtain a resin in which Fmoc group protection is removed;

(c) condensation of amino acids: N-α-Fmoc protected amino acid Fmoc-AA-OH, N-hydroxybenzotriazole and O-benzotriazole-N,N,N',N' tetramethylurea-hexafluorophosphate are completely dissolved in DMF in turn, and then diisopropylethylamine is added, mixed to obtain a mixed solution; then added into the resin in which the Fmoc group protection is removed and stirred for 60 min in argon, and the solvent is evaporated; repeatedly washed with DMF, and evaporated, and the Fmoc group protection is removed according to the process in step (b) to obtain a peptide resin in which the Fmoc protecting group is removed; the molar ratio of Fmoc-AA-OH and the resin in which the Fmoc group protection is removed is 1:2 to 1:5; the molar ratio of N-α-Fmoc protected amino acid Fmoc-AA-OH, N-hydroxybenzotriazole, O-benzotriazole-N,N,N',N'-tetramethylurea-hexafluorophosphate and diisopropylethylamine is 1:1:1:2;

(d) extension of the peptide chain: according to the structural design of the polypeptide, the N-α-Fmoc protected amino acid is selected from the C-terminus in turn, and the resin in which the Fmoc protecting group is removed is subjected to the condensation of the peptide chain according to step (c) to obtain a side chain fully protected peptide resin;

(e) cleavage of the peptide chain from the resin: the peptide resin obtained in step (d) is washed alternately with DCM and MeOH, and the solvent is sufficiently evaporated, then a cleavage agent is added, and incubated for 2 to 3 hours at room temperature; filtered, and the filtrate is sufficiently evaporated under reduced pressure at a temperature not higher than 37° C., and then precipitated with ethyl ether at not higher than −10° C.; the supernatant is aspirated, water is added to sufficiently dissolve the precipitate, the ethyl ether is removed from the aqueous phase, and the aqueous phase is freeze-dried to obtain a white crude peptide solid powder; the cleavage agent is a solution formed by mixing trifluoroacetic acid, triisopropylsilane and water at a volume ratio of 95:2.5:2.5; the cleavage agent is added in an amount of 18 ml of a cleavage agent per gram of the peptide resin; and (f) desalination and purification of the polypeptide: acetic acid solution with a volume concentration of 15-20% is used as a mobile phase, passed through a Sephadex G25 cross-linked dextran gel column; the main peak is collected by a UV detector and then freeze-dried to obtain a desalted peptide compound; and then the desalted peptide compound is separated and purified by reversed-phase high-performance liquid chromatography column, and the main peak of the sample is collected after separation to obtain the multi-target polypeptide product.

3. A method for treating pain comprising administering to a subject in need thereof a therapeutically effective amount of the multi-target polypeptide of opioid and neuropeptide FF receptors of claim 1.

* * * * *